United States Patent
Wang et al.

(10) Patent No.: US 12,232,801 B2
(45) Date of Patent: Feb. 25, 2025

(54) SYSTEM AND METHOD FOR MITIGATING RISING IMPEDANCE VIA A PUMP ASSEMBLY DURING USE OF COOLED RADIOFREQUENCY PROBES

(71) Applicant: Avent, Inc., Alpharetta, GA (US)

(72) Inventors: Ruoya Wang, Decatur, GA (US); Jennifer J. Barrett, Alpharetta, GA (US); Joseph DiPietro, Ponte Vedra, FL (US); Rasagnya M. Viswanadha, Cumming, GA (US); Tyler W. Crone, Atlanta, GA (US)

(73) Assignee: Avent, Inc., Alpharetta, GA (US)

( * ) Notice: Subject to any disclaimer, the term of this patent is extended or adjusted under 35 U.S.C. 154(b) by 1123 days.

(21) Appl. No.: 17/058,718

(22) PCT Filed: May 28, 2019

(86) PCT No.: PCT/US2019/034164
§ 371 (c)(1),
(2) Date: Nov. 25, 2020

(87) PCT Pub. No.: WO2019/231907
PCT Pub. Date: Dec. 5, 2019

(65) Prior Publication Data
US 2021/0169556 A1 Jun. 10, 2021

Related U.S. Application Data

(60) Provisional application No. 62/677,714, filed on May 30, 2018.

(51) Int. Cl.
*A61B 18/12* (2006.01)
*A61B 18/14* (2006.01)
*A61B 18/00* (2006.01)

(52) U.S. Cl.
CPC .. *A61B 18/148* (2013.01); *A61B 2018/00023* (2013.01); *A61B 2018/00077* (2013.01);
(Continued)

(58) Field of Classification Search
CPC ........ A61B 18/148; A61B 2018/00023; A61B 2018/00077; A61B 2018/00083;
(Continued)

(56) References Cited

U.S. PATENT DOCUMENTS

| 5,437,662 A | 8/1995 | Nardella |
| 6,231,570 B1 | 5/2001 | Tu et al. |

(Continued)

FOREIGN PATENT DOCUMENTS

| EP | 2 875 791 A1 | 5/2015 |
| EP | 1493397 B2 | 7/2015 |

(Continued)

OTHER PUBLICATIONS

International Search Report and Written Opinion for PCT/US2019/034164, dated Jul. 31, 2019, 14 pages.

(Continued)

*Primary Examiner* — Michael F Peffley
*Assistant Examiner* — Amanda L Zink
(74) *Attorney, Agent, or Firm* — Meunier Carlin & Curfman LLC

(57) ABSTRACT

A method of treating tissue of a patient's body includes providing a power source coupled to at least one probe assembly. The probe assembly includes an elongate member with a distal region and a proximal region. The distal region has an electrically and thermally-conductive energy delivery device for delivering one of electrical and radiofrequency energy to the patient's body. The electrically and thermally-conductive energy delivery device has one or more internal (Continued)

lumens for circulating a cooling fluid therethrough and an electrically and thermally-conductive protrusion having a temperature sensing element. The temperature sensing element extends from a distal end of the energy delivery device. The method includes inserting the energy delivery device of the at least one probe assembly into the patient's body. Further, the method includes routing the energy delivery device of the at least one probe assembly to the tissue of the patient's body. The method also includes simultaneously circulating the cooling fluid through the one or more internal lumens via at least one pump assembly and delivering energy from the power source to the tissue through the energy delivery device. Further, the method includes monitoring one or more procedure parameters while delivering the energy from the power source to the tissue through the energy delivery device. Moreover, the method includes determining, in real-time, whether a rising impedance event is likely to occur in a predetermined time period based on the one or more procedure parameters and determining a command for the pump assembly based on whether the rising impedance event is likely to occur in the predetermined time period.

17 Claims, 16 Drawing Sheets

(52) U.S. Cl.
CPC ............... *A61B 2018/00083* (2013.01); *A61B 2018/00095* (2013.01); *A61B 2018/00339* (2013.01); *A61B 2018/00434* (2013.01); *A61B 2018/00577* (2013.01); *A61B 2018/00589* (2013.01); *A61B 2018/00678* (2013.01); *A61B 2018/00797* (2013.01); *A61B 2018/00875* (2013.01)

(58) Field of Classification Search
CPC ........... A61B 2018/00095; A61B 2018/00339; A61B 2018/00434; A61B 2018/0044; A61B 2018/00577; A61B 2018/00589; A61B 2018/00678; A61B 2018/00797; A61B 2018/00815; A61B 2018/00821; A61B 2018/00875
See application file for complete search history.

(56) References Cited

U.S. PATENT DOCUMENTS

| | | | |
|---|---|---|---|
| 6,413,254 B1 | 7/2002 | Hissong et al. | |
| 6,425,912 B1 | 7/2002 | Knowlton | |
| 6,575,969 B1 | 6/2003 | Rittman, III et al. | |
| 7,048,732 B2 | 5/2006 | Ellingsen | |
| 7,081,111 B2 | 7/2006 | Svaasand et al. | |
| 7,108,696 B2 | 9/2006 | Daniel et al. | |
| 7,160,296 B2 | 1/2007 | Pearson et al. | |
| 7,201,750 B1 | 4/2007 | Eggers et al. | |
| 7,247,155 B2 | 7/2007 | Hoey et al. | |
| 7,344,533 B2 | 3/2008 | Pearson et al. | |
| 7,771,420 B2 | 8/2010 | Butty et al. | |
| 7,818,854 B2 | 10/2010 | Wilson | |
| 7,976,537 B2 | 7/2011 | Lieber et al. | |
| 8,764,744 B2 | 7/2014 | Brannan | |
| 8,932,288 B2 | 1/2015 | Leo et al. | |
| 8,971,997 B2 | 3/2015 | Oral et al. | |
| 9,078,680 B2 | 7/2015 | Lemberg et al. | |
| 9,138,288 B2 | 9/2015 | Curley | |
| 9,326,813 B2 | 5/2016 | Pike, Jr. et al. | |
| 9,333,024 B2 | 5/2016 | Woloszko et al. | |
| 9,420,955 B2 | 8/2016 | Weber | |
| 9,956,032 B1 | 5/2018 | Cosman et al. | |
| 2002/0111615 A1* | 8/2002 | Cosman | A61B 18/14 606/41 |
| 2005/0107778 A1* | 5/2005 | Rioux | A61B 18/148 606/41 |
| 2005/0177210 A1 | 8/2005 | Leung et al. | |
| 2005/0177211 A1* | 8/2005 | Leung | A61B 18/148 607/101 |
| 2005/0209578 A1 | 9/2005 | Christian Evans et al. | |
| 2006/0200121 A1 | 9/2006 | Mowery | |
| 2007/0078502 A1 | 4/2007 | Weber et al. | |
| 2007/0287995 A1 | 12/2007 | Mayse | |
| 2008/0009747 A1 | 1/2008 | Saadat et al. | |
| 2009/0163807 A1 | 6/2009 | Sliwa | |
| 2009/0287092 A1 | 11/2009 | Leo et al. | |
| 2011/0077628 A1 | 3/2011 | Hoey et al. | |
| 2011/0288540 A1 | 11/2011 | Wright et al. | |
| 2012/0172858 A1 | 7/2012 | Harrison et al. | |
| 2014/0081260 A1 | 3/2014 | Cosman, Jr. et al. | |
| 2015/0105701 A1 | 4/2015 | Mayer et al. | |
| 2015/0313699 A1 | 11/2015 | Darmos et al. | |
| 2015/0320473 A1 | 11/2015 | Kalser et al. | |
| 2016/0206370 A1 | 7/2016 | Fruland et al. | |
| 2017/0020606 A1 | 1/2017 | Leung et al. | |
| 2017/0065335 A1 | 3/2017 | Wright et al. | |
| 2018/0078170 A1 | 3/2018 | Panescu et al. | |

FOREIGN PATENT DOCUMENTS

| | | |
|---|---|---|
| GB | 2 210 560 A | 6/1989 |
| WO | WO 99/04710 A1 | 2/1999 |
| WO | WO 01/33165 A1 | 5/2001 |
| WO | WO 2006/021095 A1 | 3/2006 |
| WO | WO 2018/067496 A1 | 4/2018 |

OTHER PUBLICATIONS

International Preliminary Report on Patentability issued in PCT/US2019/034164 on Dec. 1, 2020, 8 pages.
Examination Report issued in Australian Application No. 2019277125 on May 3, 2024, 4 pages.

* cited by examiner

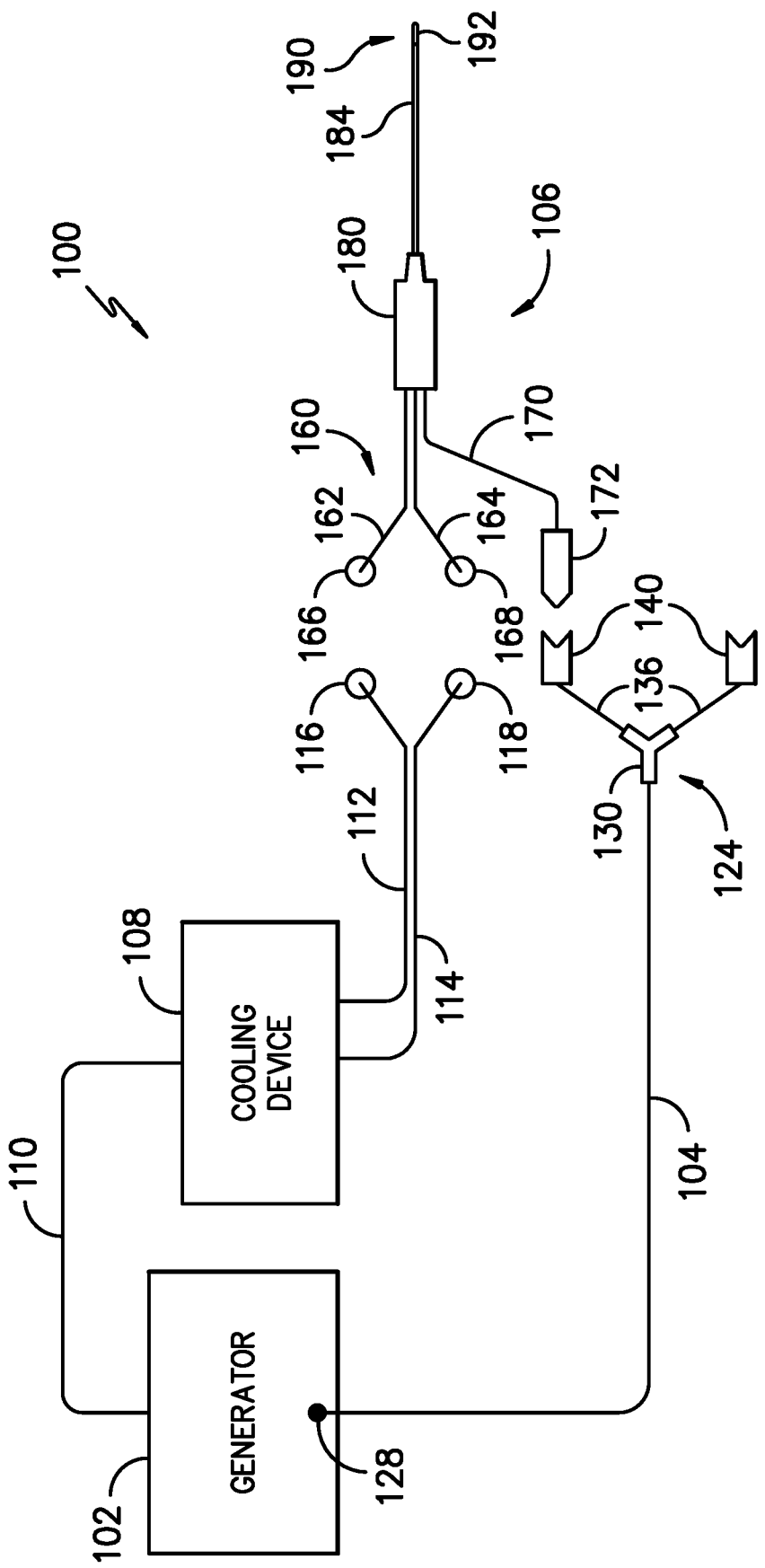
FIG. -1-

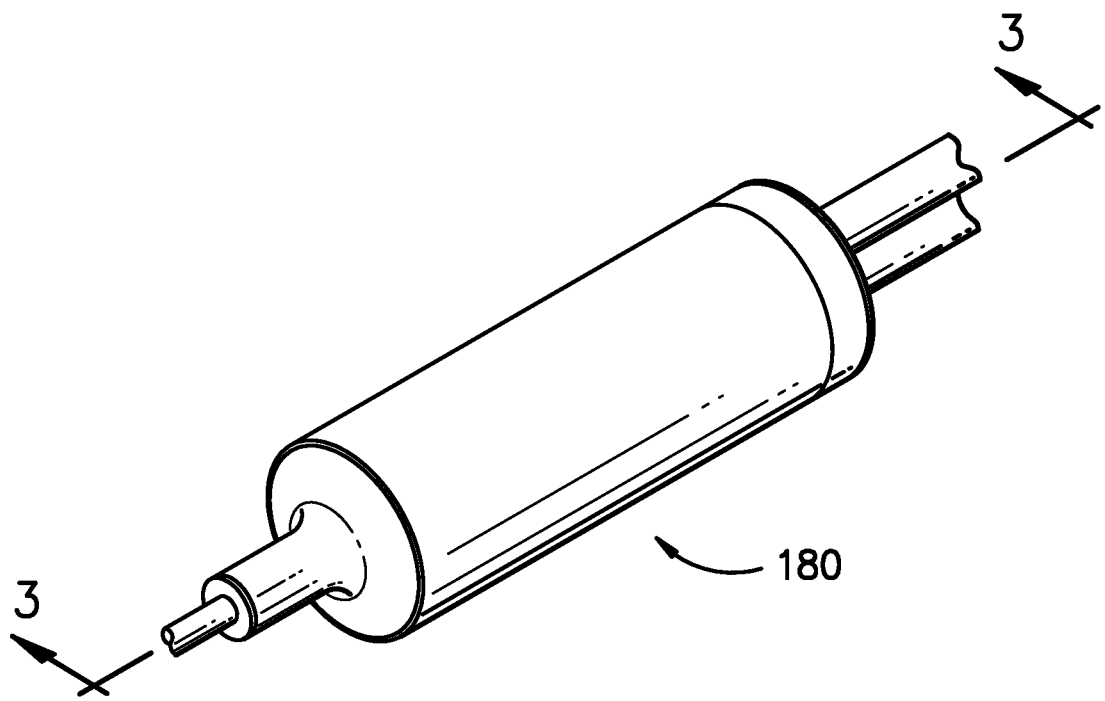
FIG. -2-
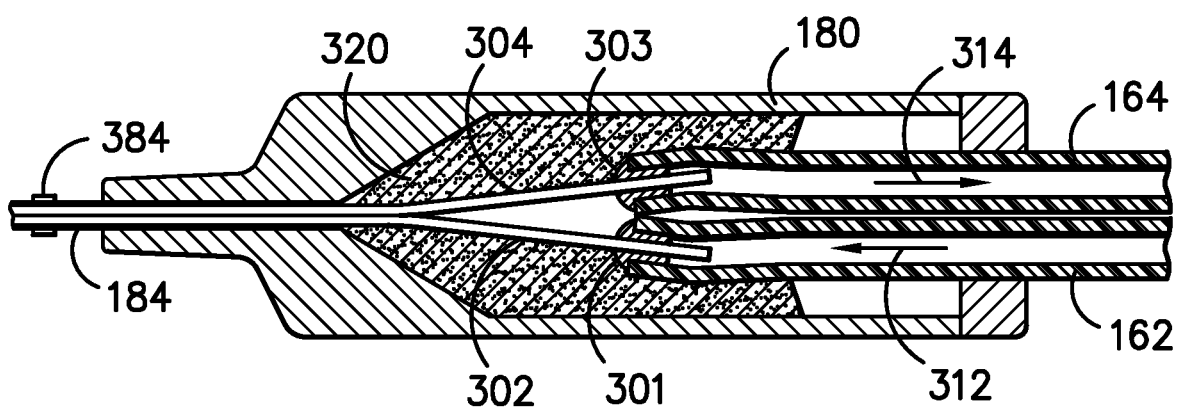
FIG. -3-

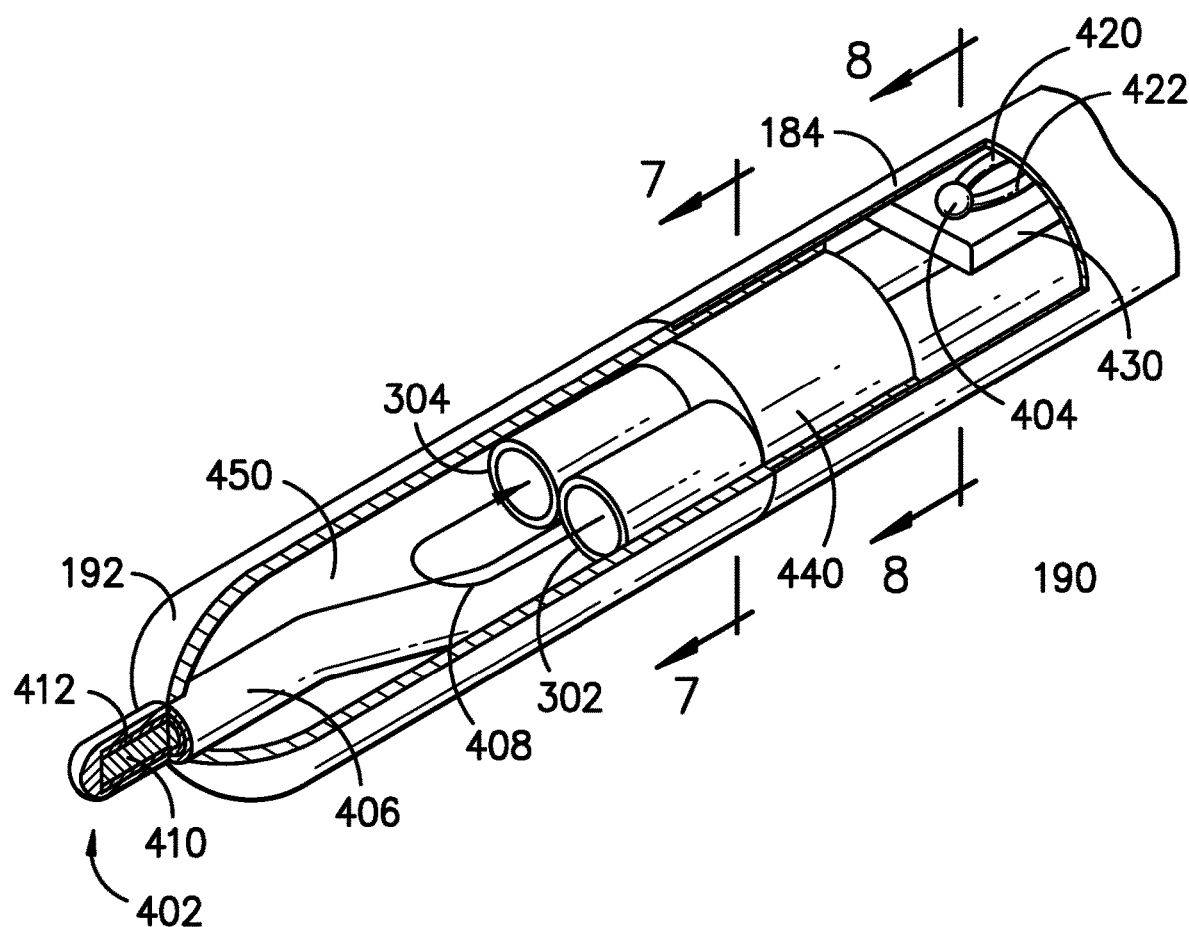
FIG. -4-

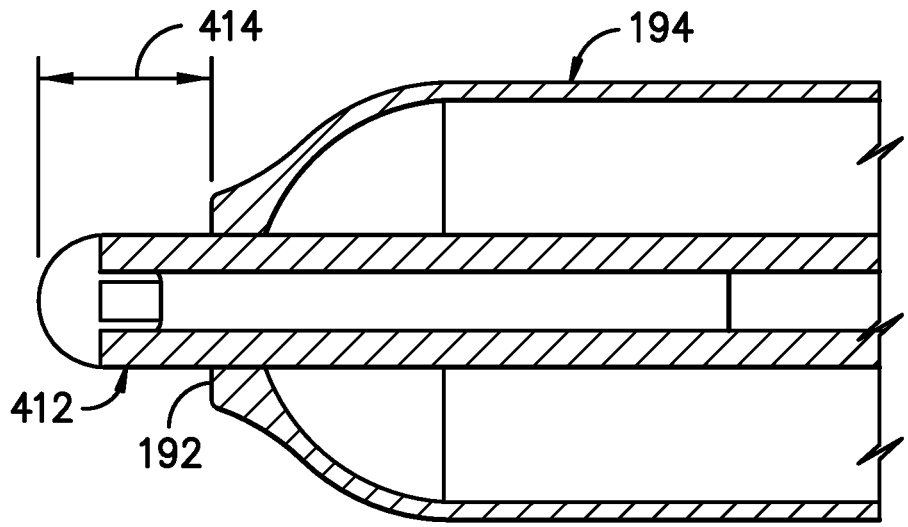
FIG. -5-
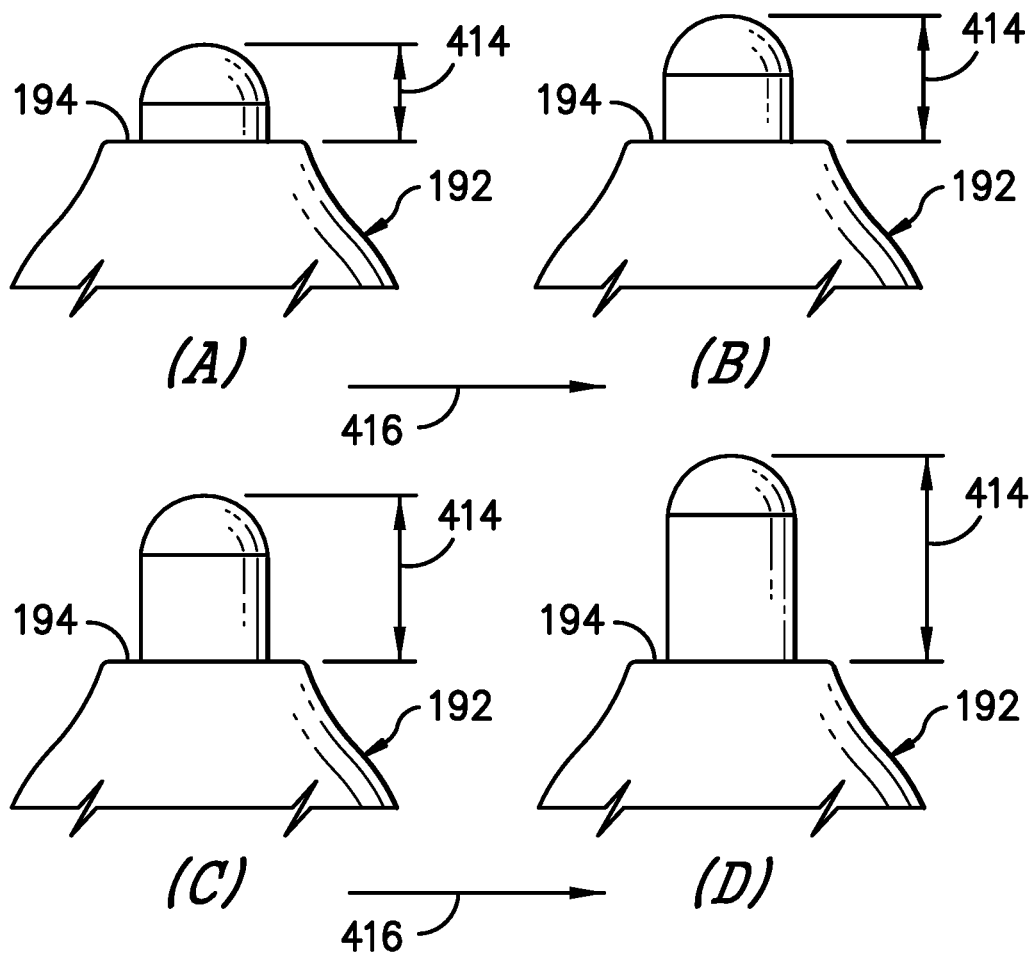
FIG. -6-

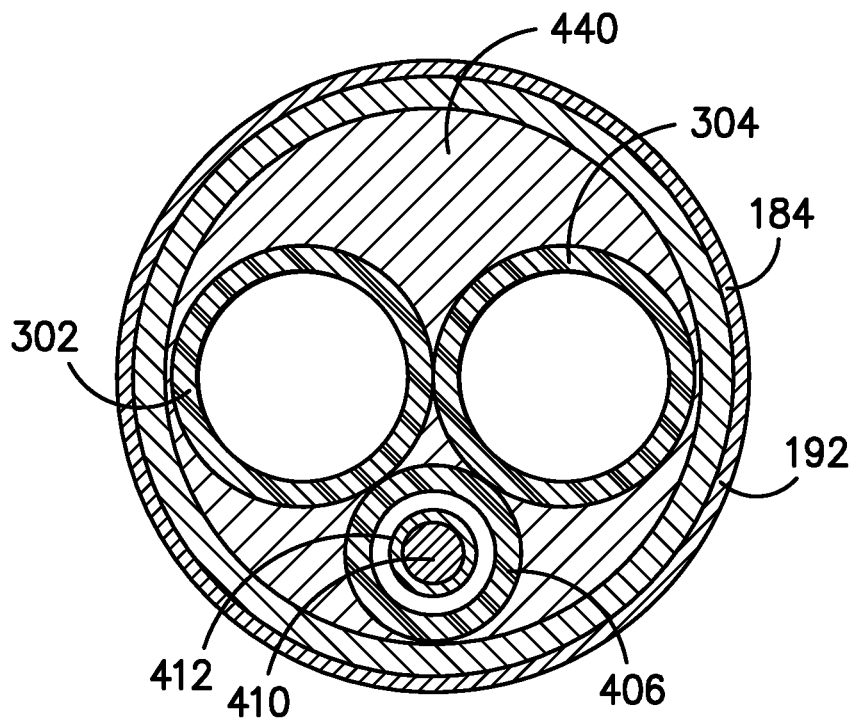
FIG. -7-
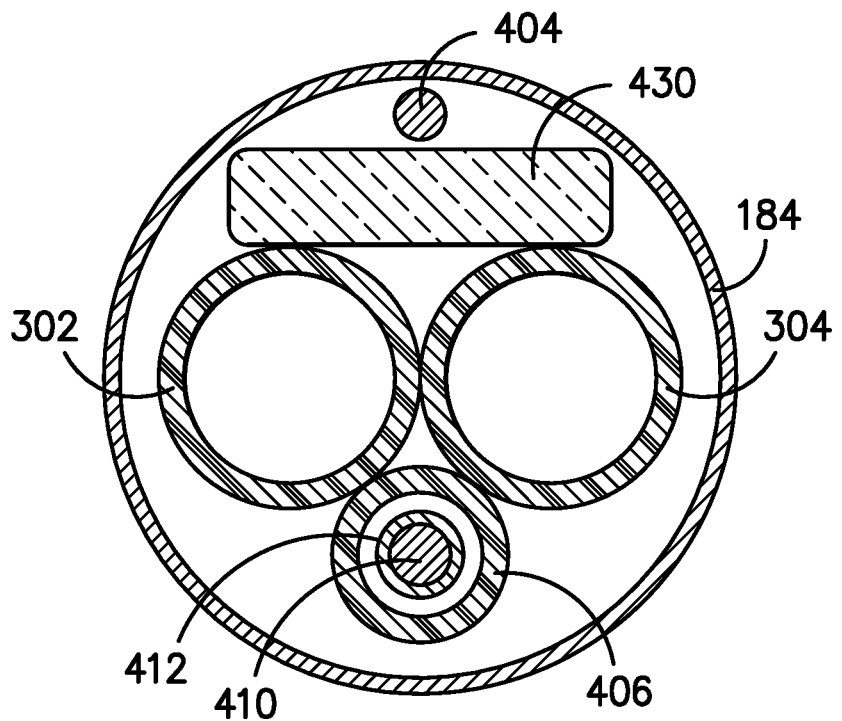
FIG. -8-

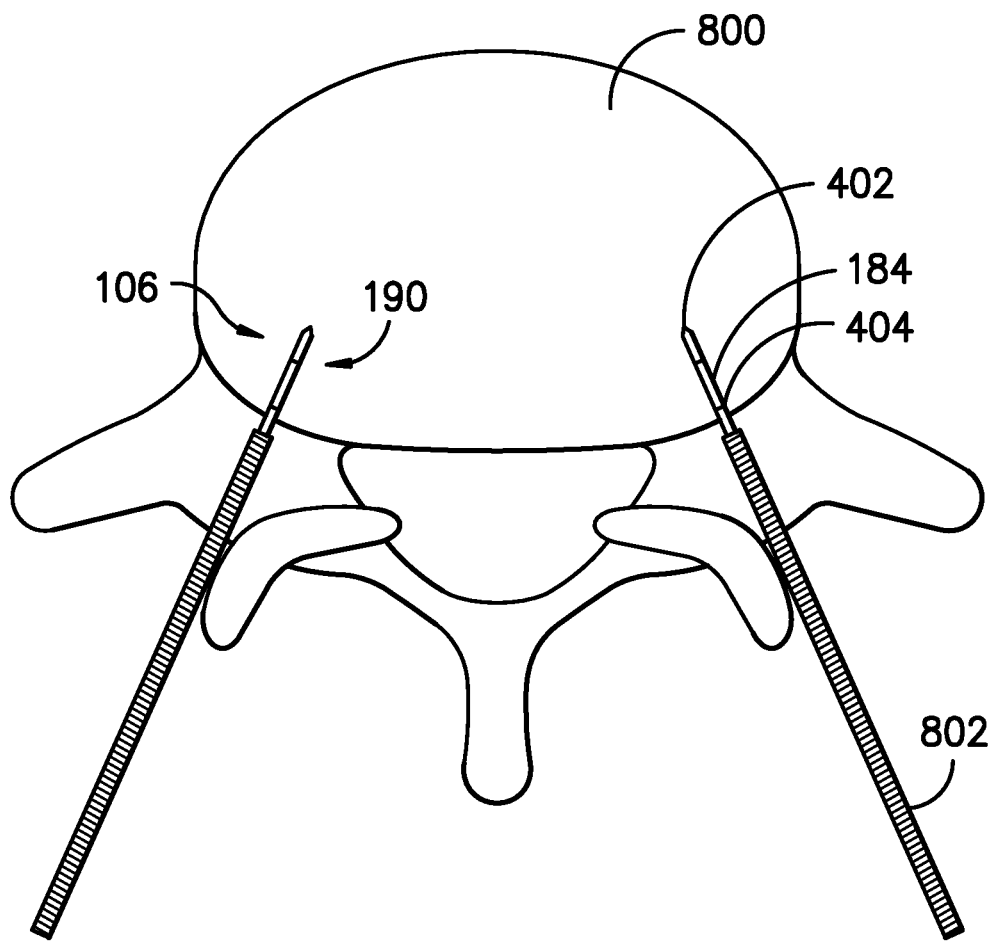
FIG. -9-

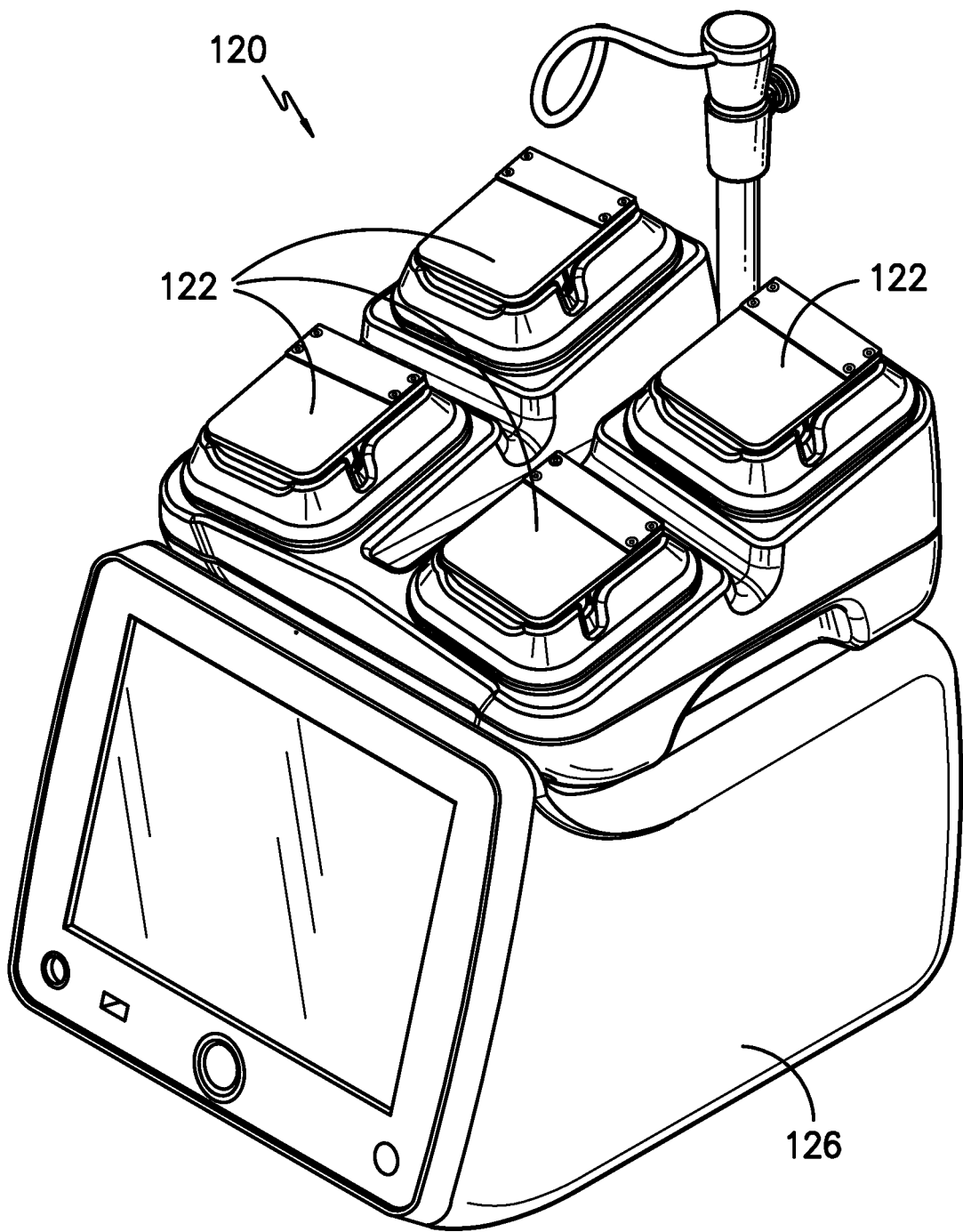
FIG. -10-

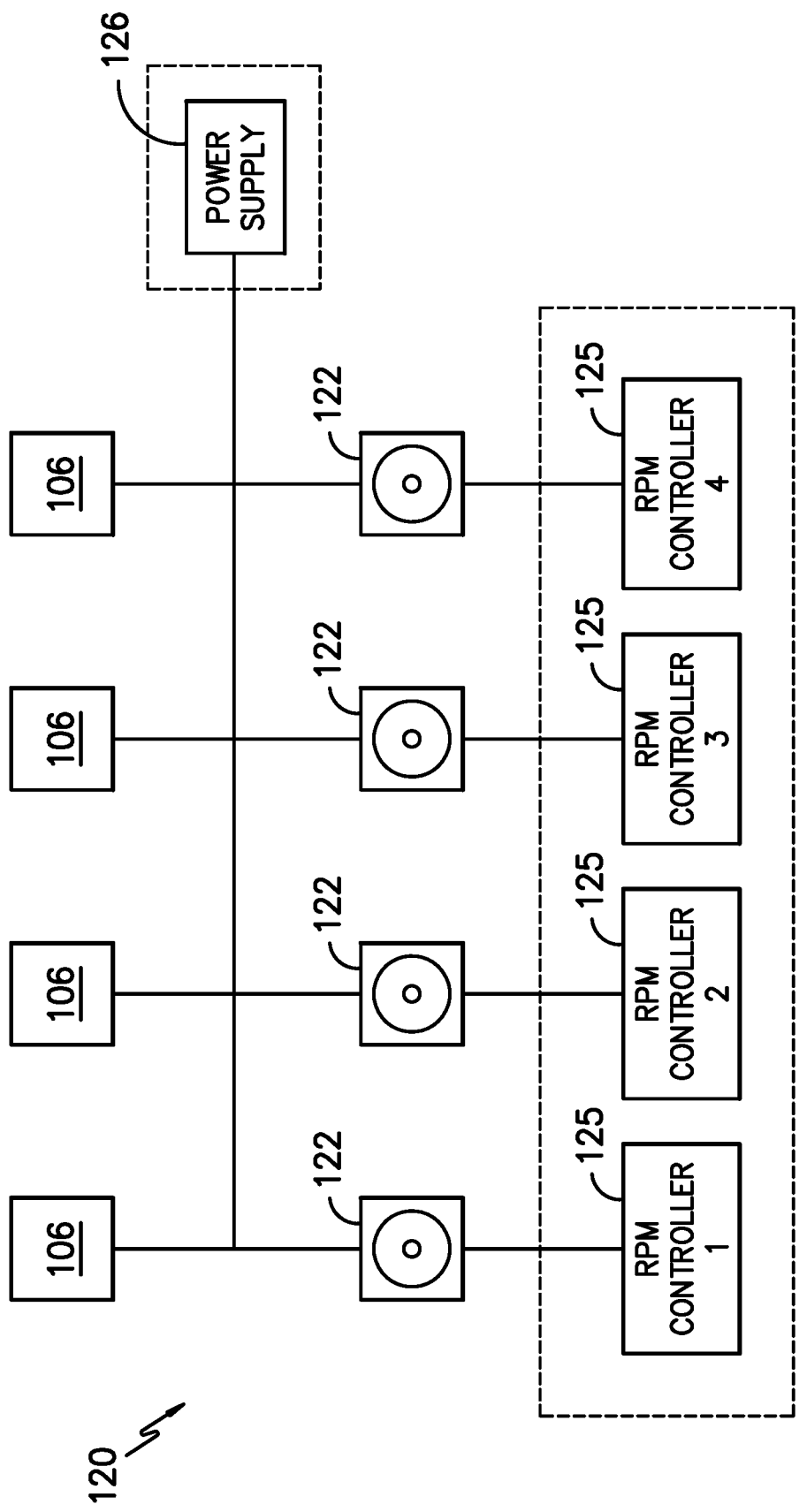

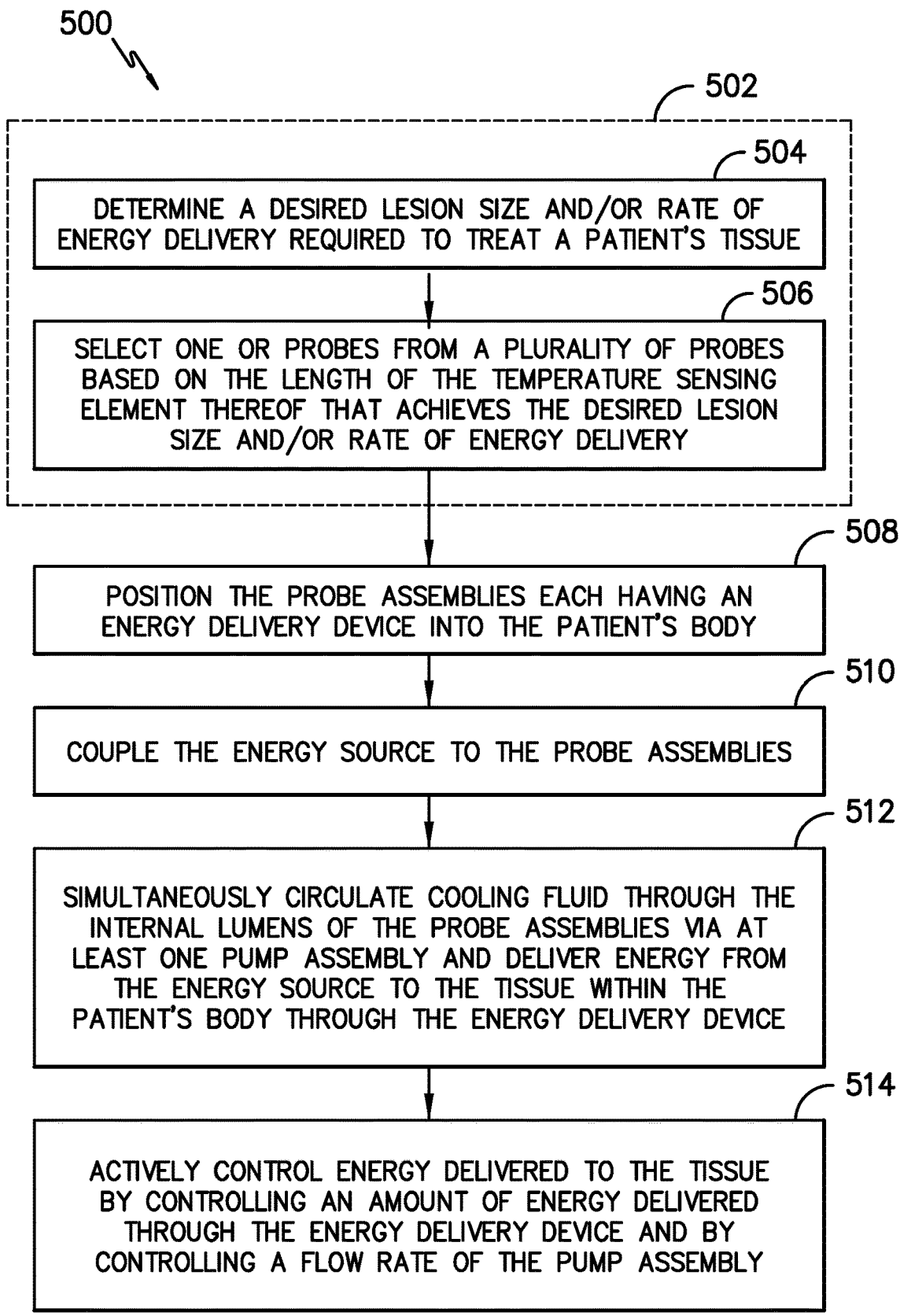
FIG. -12-

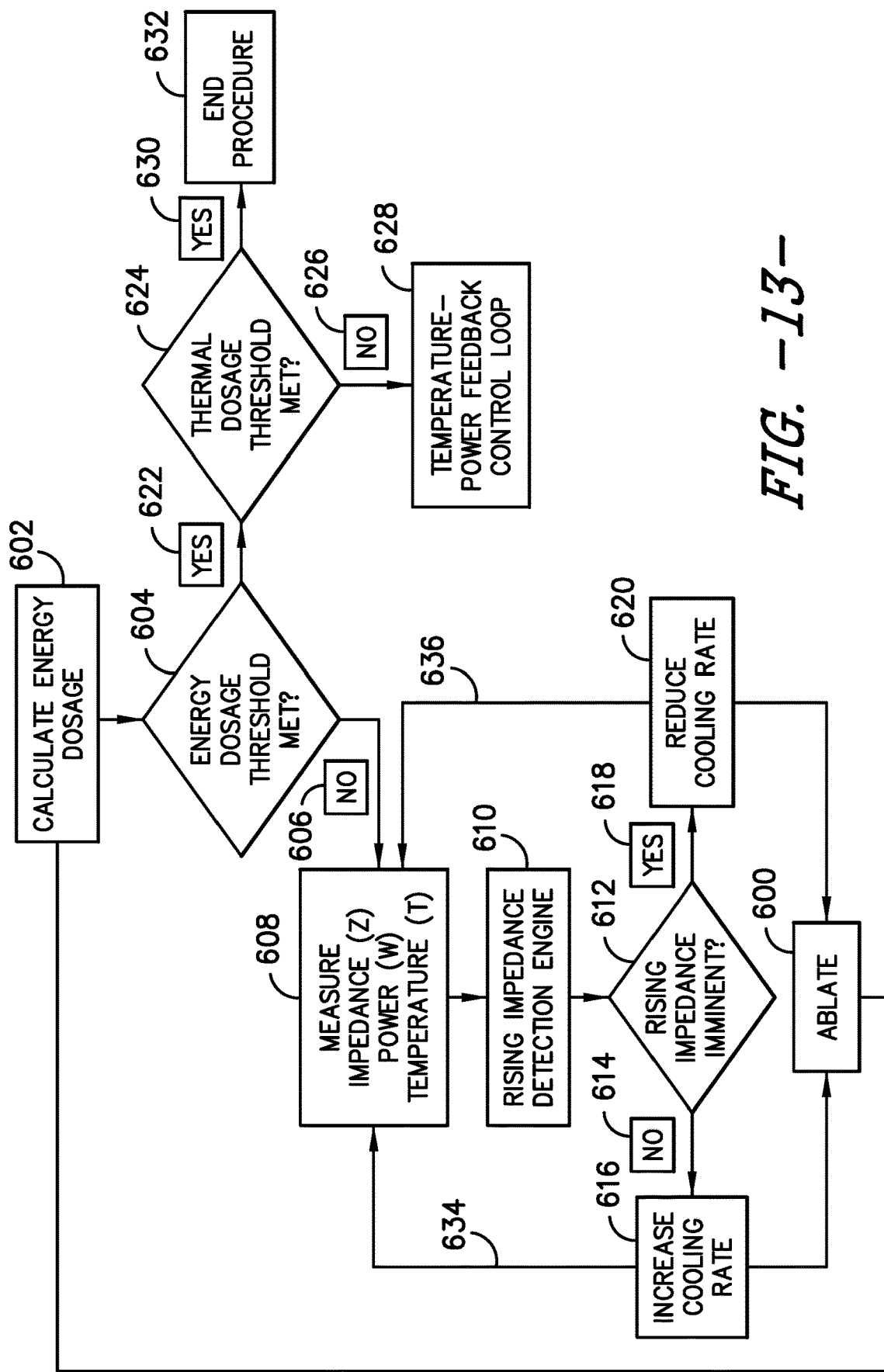
FIG. -13-

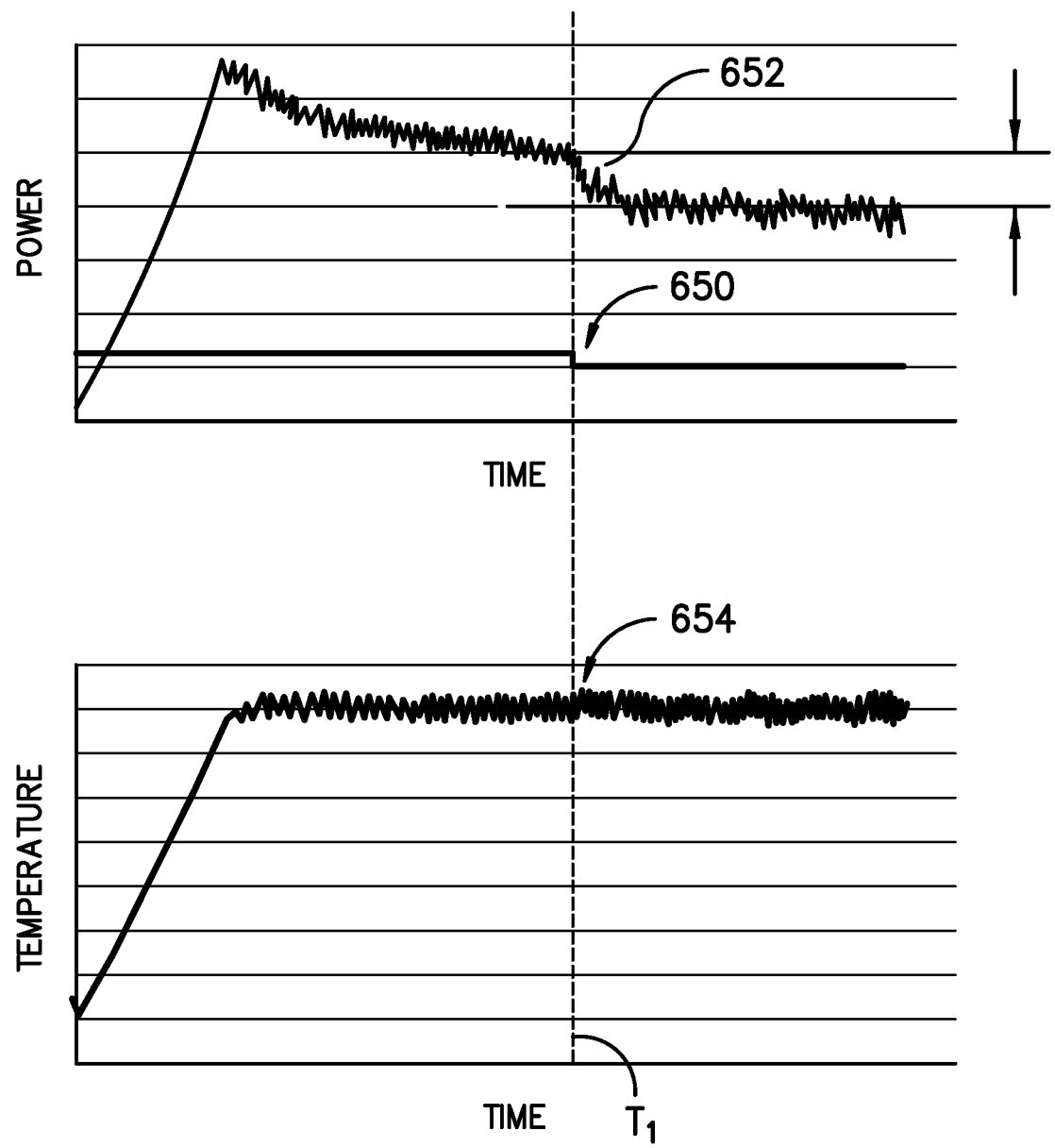
FIG. -14-

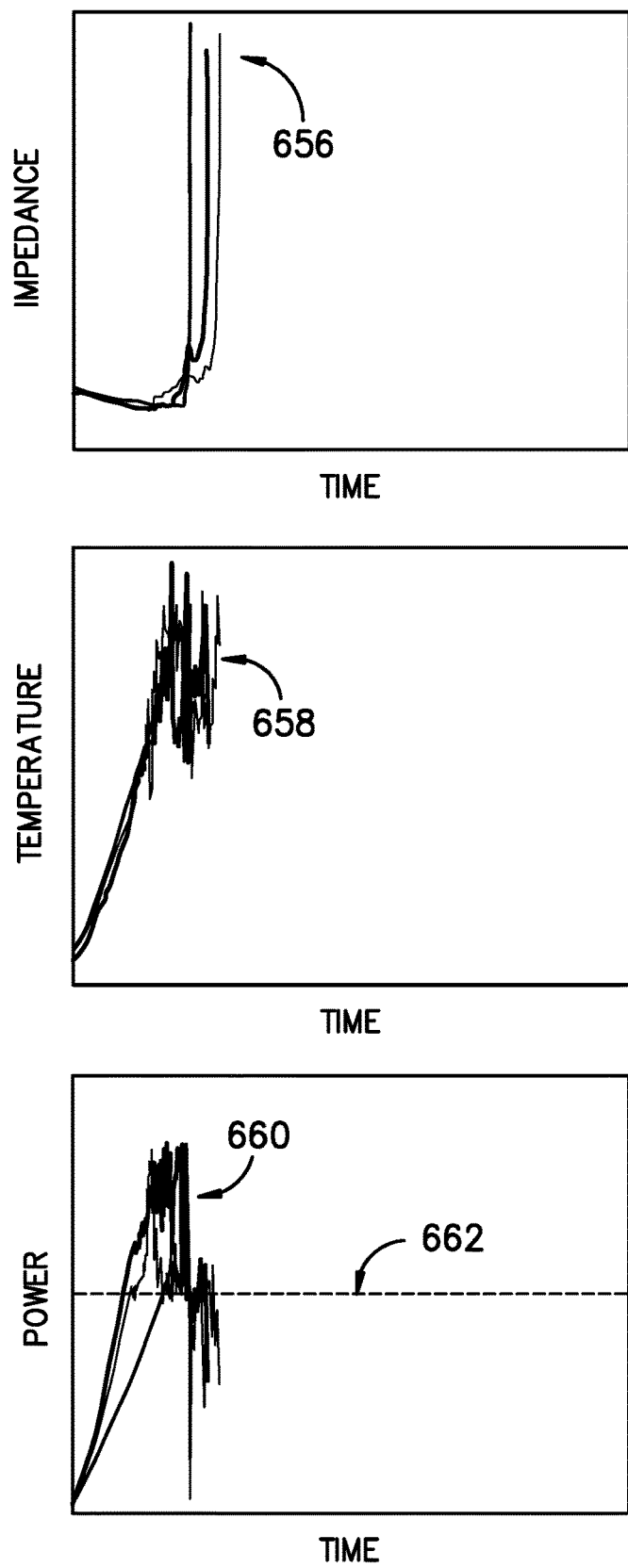
FIG. -15-

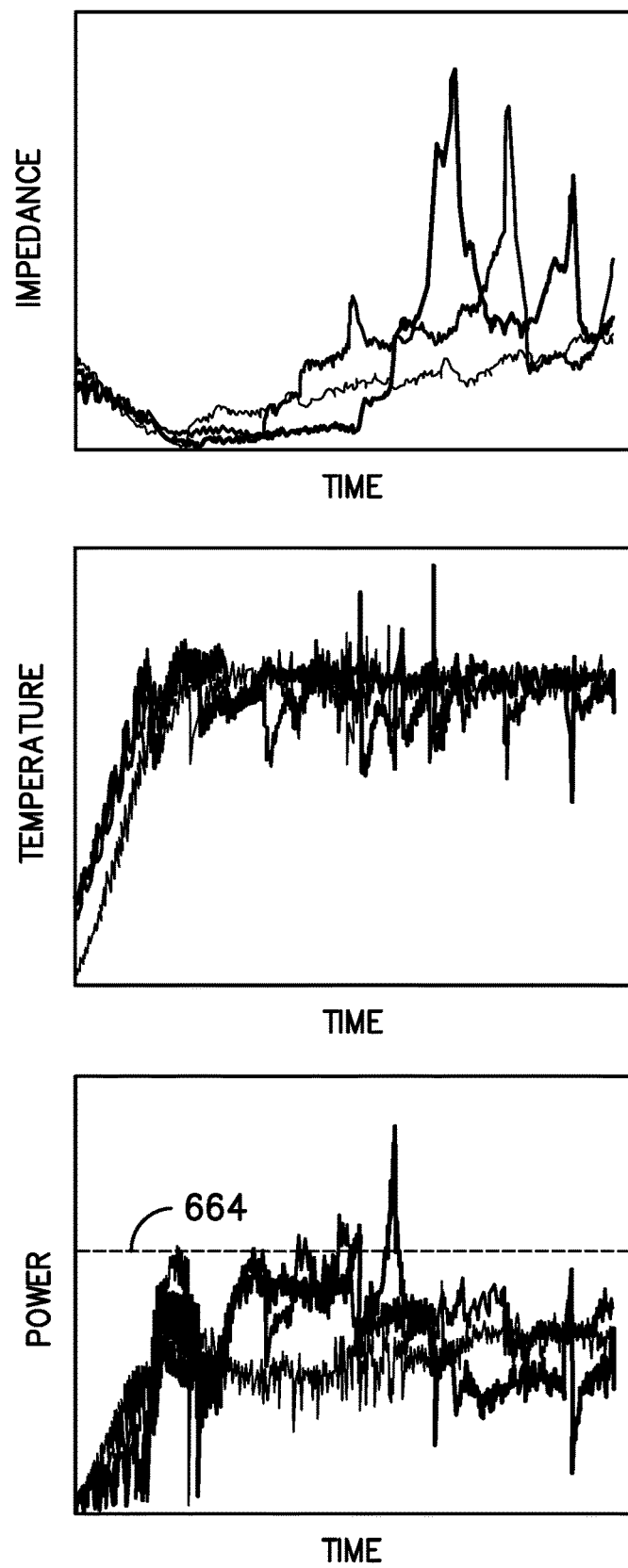
FIG. -16-

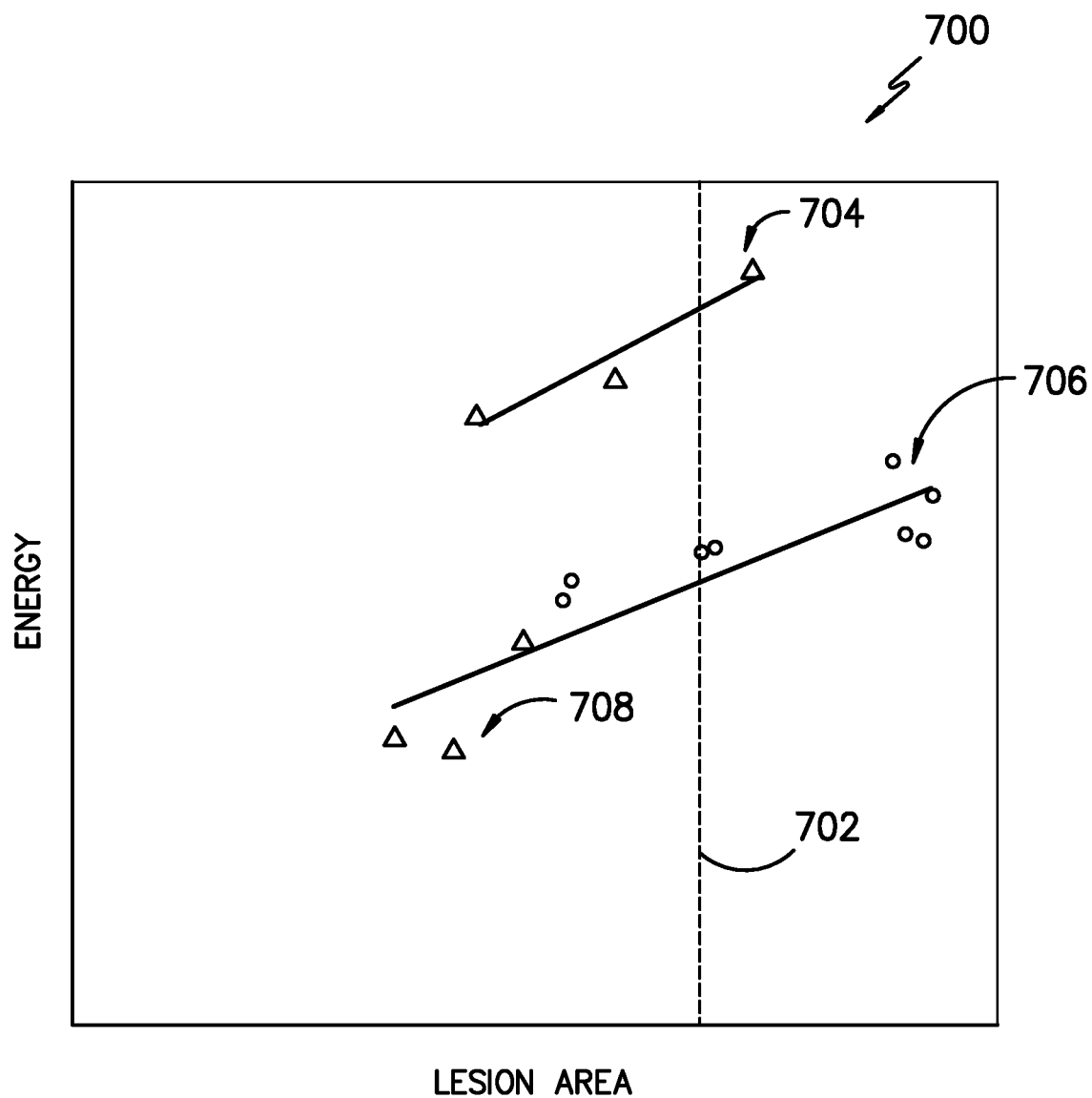
FIG. -17-

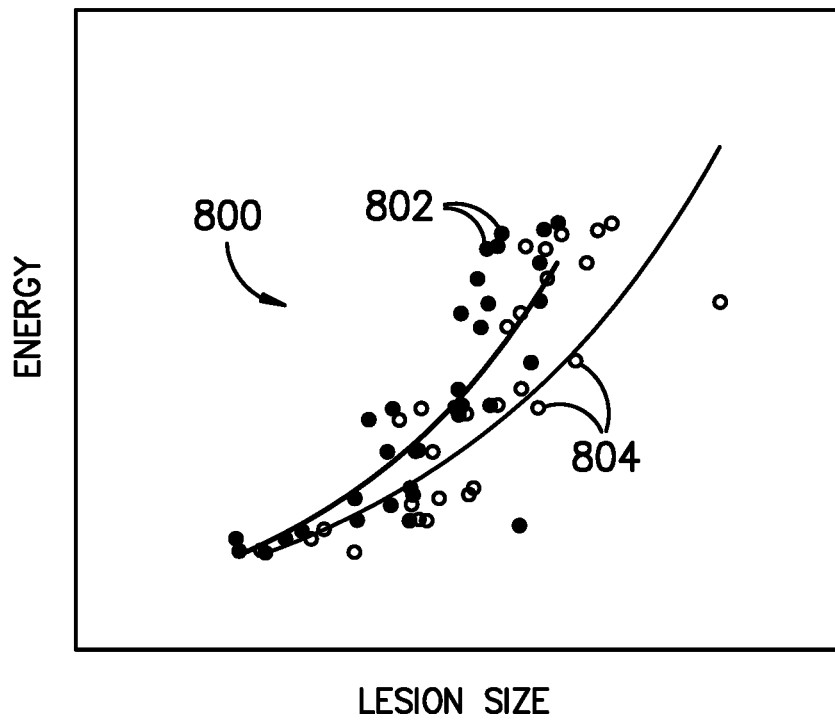
LESION SIZE
FIG. -18-
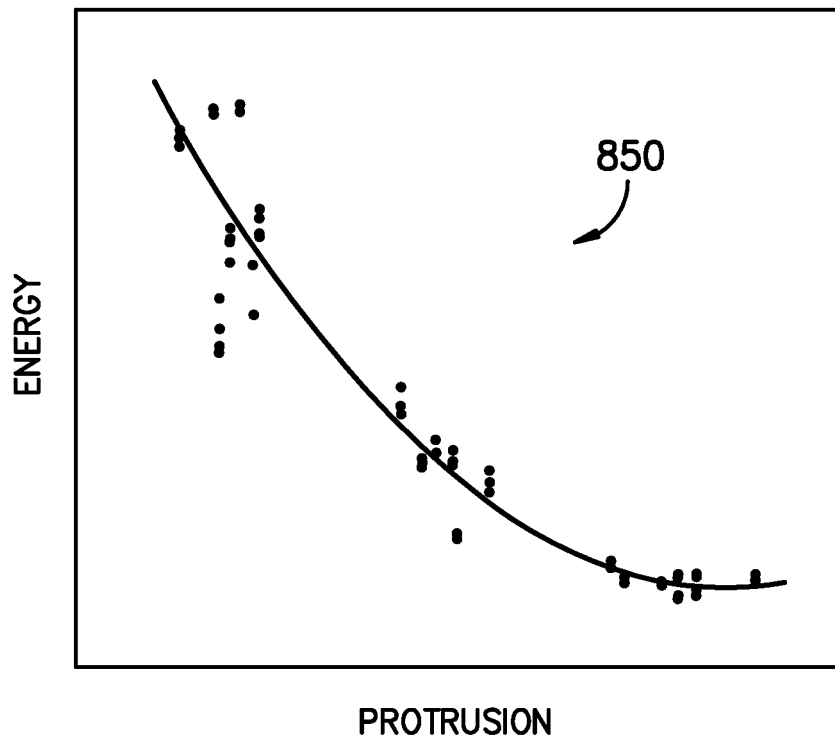
PROTRUSION
FIG. -19-

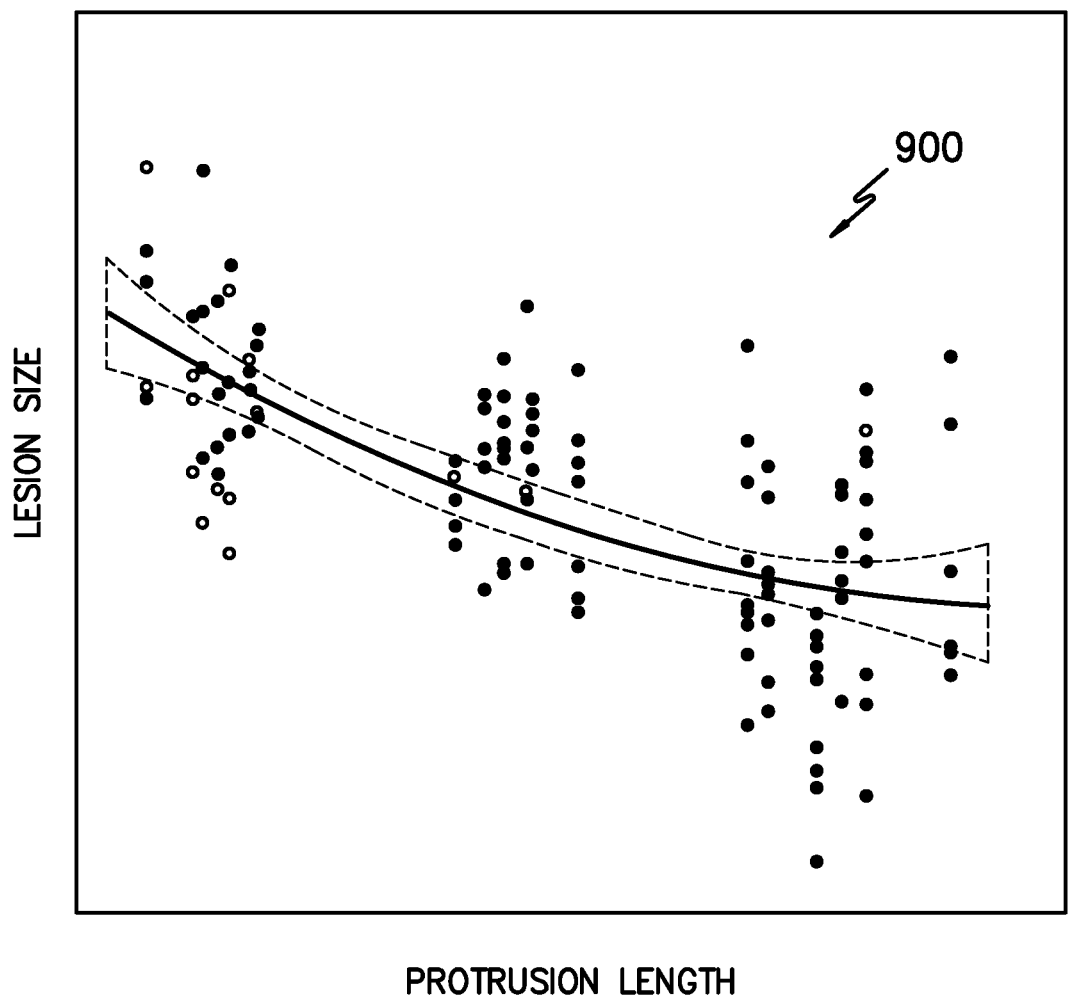
FIG. -20-

SYSTEM AND METHOD FOR MITIGATING RISING IMPEDANCE VIA A PUMP ASSEMBLY DURING USE OF COOLED RADIOFREQUENCY PROBES

RELATED APPLICATIONS

The present invention claims priority to U.S. Provisional Application No.: 62/677,714 filed on May 30, 2018, which is incorporated herein by reference in its entirety.

FIELD OF THE INVENTION

The present invention relates generally to a system and method for applying energy for the treatment of tissue, and more particularly to a system and method for mitigating rising impedance via a pump assembly during use of cooled radiofrequency probes.

BACKGROUND

Lower back injuries and chronic joint pain are major health problems resulting not only in debilitating conditions for the patient, but also in the consumption of a large proportion of funds allocated for health care, social assistance and disability programs. In the lower back, disc abnormalities and pain may result from trauma, repetitive use in the workplace, metabolic disorders, inherited proclivity, and/or aging. The existence of adjacent nerve structures and innervation of the disc are very important issues in respect to patient treatment for back pain. In joints, osteoarthritis is the most common form of arthritis pain and occurs when the protective cartilage on the ends of bones wears down over time.

A minimally invasive technique of delivering high-frequency electrical current has been shown to relieve localized pain in many patients. Generally, the high-frequency current used for such procedures is in the radiofrequency (RF) range, i.e. between 100 kHz and 1 GHz and more specifically between 300-600 kHz. The RF electrical current is typically delivered from a generator via connected electrodes that are placed in a patient's body, in a region of tissue that contains a neural structure suspected of transmitting pain signals to the brain. The electrodes generally include an insulated shaft with an exposed conductive tip to deliver the radiofrequency electrical current. Tissue resistance to the current causes heating of tissue adjacent resulting in the coagulation of cells (at a temperature of approximately 45° C. for small unmyelinated nerve structures) and the formation of a lesion that effectively denervates the neural structure in question. Denervation refers to a procedure whereby the ability of a neural structure to transmit signals is affected in some way and usually results in the complete inability of a neural structure to transmit signals, thus removing the pain sensations. This procedure may be done in a monopolar mode where a second dispersive electrode with a large surface area is placed on the surface of a patient's body to complete the circuit, or in a bipolar mode where a second radiofrequency electrode is placed at the treatment site. In a bipolar procedure, the current is preferentially concentrated between the two electrodes.

To extend the size of a lesion, radiofrequency treatment may be applied in conjunction with a cooling mechanism, whereby a cooling means is used to reduce the temperature of the tissue near an energy delivery device, allowing a higher power to be applied without causing an unwanted increase in local tissue temperature. The application of a higher power allows regions of tissue further away from the energy delivery device to reach a temperature at which a lesion can form, thus increasing the size/volume of the lesion.

The treatment of pain using high-frequency electrical current has been applied successfully to various regions of patients' bodies suspected of contributing to chronic pain sensations. For example, with respect to back pain, which affects millions of individuals every year, high-frequency electrical treatment has been applied to several tissues, including intervertebral discs, facet joints, sacroiliac joints as well as the vertebrae themselves (in a process known as intraosseous denervation). In addition to creating lesions in neural structures, application of radiofrequency energy has also been used to treat tumors throughout the body. Further, with respect to knee pain, which also affects millions of individuals every year, high-frequency electrical treatment has been applied to several tissues, including, for example, the ligaments, muscles, tendons, and menisci.

In certain instances, internally-cooled radiofrequency probes may be susceptible to rising impedance issues, which can prematurely terminate the ablation procedure. More specifically, as the impedance rises, it becomes increasing more difficult to effectively transfer the radiofrequency energy to the tissue and create heat. This can lead to poorly formed lesions, procedural complications, and/or customer dissatisfaction. Such rising impedance issues may be caused due to the inherent higher power demands of internally-cooled radiofrequency probes and/or the difficulty in measuring and controlling to the highest lesion temperature. Rising impedance occurs when excessive heat is generated in the tissue surrounding the active electrode, thereby causing desiccation of the tissue, migration of surrounding conductive ions, and/or accumulation of a carbonized tissue layer around the active tip. Such effects can result in rising impedance by acting as an electrical insulator between the active electrode and the surrounding tissue.

Thus, the art is continuously seeking new and improved systems and methods for treating chronic pain using cooled RF ablation techniques that also consider the aforementioned rising impedance issues.

SUMMARY OF THE INVENTION

Objects and advantages of the invention will be set forth in part in the following description, or may be obvious from the description, or may be learned through practice of the invention.

In one aspect, the present invention is directed to a method of treating tissue of a patient's body. The method includes providing a power source coupled to at least one probe assembly. The probe assembly includes an elongate member with a distal region and a proximal region. The distal region has an electrically and thermally-conductive energy delivery device for delivering one of electrical and radiofrequency energy to the patient's body. The electrically and thermally-conductive energy delivery device has one or more internal lumens for circulating a cooling fluid therethrough and an electrically and thermally-conductive protrusion having a temperature sensing element. The temperature sensing element extends from a distal end of the energy delivery device. The method includes inserting the energy delivery device of the at least one probe assembly into the patient's body. Further, the method includes routing the energy delivery device of the at least one probe assembly to the tissue of the patient's body. The method also includes simultaneously circulating the cooling fluid through the one or more internal lumens via at least one pump assembly and delivering energy from the power source to the tissue through the energy delivery device. Further, the method includes monitoring one or more procedure parameters while delivering the energy from the power source to the tissue through the energy delivery device. Moreover, the method includes determining, in real-time, whether a rising impedance event is likely to occur in a predetermined time period based on the one or more procedure parameters. In addition, the method includes determining a command for the pump assembly based on whether the rising impedance event is likely to occur in the predetermined time period.

In one embodiment, if the rising impedance event is likely to occur in the predetermined time period, the step of determining the command for the pump assembly may include decreasing a flow rate of the pump assembly. Alternatively, if the rising impedance event is unlikely to occur in the predetermined time period, the step of determining the command for the pump assembly may include increasing the flow rate of the pump assembly up to a predetermined maximum flow rate or rotational speed.

In another embodiment, the procedure parameter(s) may include a temperature of the tissue, an impedance of the tissue, a power demand of the energy delivery device, or similar, or combinations thereof.

In further embodiments, the method may include measuring the temperature of the tissue using the temperature sensing element. In such embodiments, the temperature sensing element may include a length of less than about 1 millimeter (mm) that extends from the distal end of the energy delivery device. In additional embodiments, the pump assembly may include at least one pump communicatively coupled to at least one control module.

In several embodiments, the method may include comparing the power demand of the energy delivery device to a predetermined threshold. If the power demand is greater than the predetermined threshold, the step of determining the command for the pump assembly may include decreasing a speed of the pump(s). If the power demand is less than the predetermined threshold, the step of determining the command for the pump assembly may include increasing the speed of the pump(s) up to a predetermined maximum flow rate or rotational speed.

In certain embodiments, the method may include decoupling, at least in part, the control module of the pump assembly from the power source.

In particular embodiments, the step of delivering energy from the power source to the tissue through the energy delivery device may include defining a predetermined threshold temperature for treating the tissue, ramping up a temperature of the tissue via the power source through the energy delivery device to the predetermined threshold temperature, and maintaining the temperature of the tissue at the predetermined threshold temperature to create a lesion in the tissue. In such embodiments, the method may include maintaining the temperature of the tissue at the predetermined threshold temperature as a function of at least one of a power ramp rate, an impedance level, an impedance ramp rate, and/or a ratio of impedance to power.

In another aspect, the present invention is directed to a medical probe assembly for delivering energy to a patient's body. The probe assembly includes at least one probe having an elongate member with a distal region and a proximal region. The distal region includes an electrically non-conductive outer circumferential portion. The probe assembly further includes an electrically and thermally-conductive energy delivery device extending distally from the electrically non-conductive outer circumferential portion for delivering one of electrical and radiofrequency energy to the patient's body. The energy delivery device includes a conductive outer circumferential surface and one or more internal lumens configured for circulating a cooling fluid to a distal end of the energy delivery device. The probe assembly also includes an electrically and thermally-conductive protrusion extending from the distal end of the energy delivery device. The electrically and thermally-conductive protrusion is electrically coupled to the energy delivery device. Further, the electrically and thermally-conductive protrusion includes a temperature sensing element. The probe assembly further includes at least one pump assembly for circulating the cooling fluid to and from the electrically and thermally-conductive energy delivery device. In addition, the probe assembly includes one or more sensors for monitoring one or more procedure parameters and a controller communicatively coupled to the sensor(s). The controller further includes a rising impedance detection engine configured to perform one or more operations, including, for example, determining, in real-time, whether a rising impedance event is likely to occur in a predetermined time period based on the one or more procedure parameters. It should also be understood that the probe assembly may further include any of the additional features as described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a portion of one embodiment of a system for applying radiofrequency electrical energy to a patient's body according to the present disclosure;

FIG. 2 illustrates an isometric view of one embodiment of the handle of the probe assembly according to the present disclosure;

FIG. 3 illustrates a longitudinal cross-section of one embodiment of a handle of the probe assembly according to the present disclosure;

FIG. 4 illustrates a perspective cut-away view of one embodiment of a distal tip region of a probe assembly according to the present disclosure;

FIG. 5 illustrates detailed, side view of the temperature sensing element of the probe assembly according to the present disclosure;

FIG. 6 illustrates side views of a plurality of temperature sensing elements of different probes according to the present disclosure, particularly illustrates temperature sensing elements each having a different length that extends from the distal end of the energy delivery device;

FIG. 7 illustrates an axial cross-sectional view through the distal tip region of the probe assembly shown in FIG. 4 along line 7-7;

FIG. 8 illustrates an axial cross-sectional view through a more proximal portion of the distal tip region of the probe assembly shown in FIG. 4 along line 8-8;

FIG. 9 illustrates two probes placed within an intervertebral disc according to the present disclosure;

FIG. 10 illustrates a perspective view of one embodiment of a pump assembly according to the present disclosure;

FIG. 11 illustrates a block diagram of one embodiment of a pump assembly according to the present disclosure;

FIG. 12 illustrates a flow diagram of one embodiment of a method of treating tissue of a patient's body according to the present disclosure;

FIG. 13 illustrates a block diagram of one embodiment of a treatment procedure for actively controlling energy delivered to tissue in the patient's body by controlling an amount of energy delivered by the energy delivery devices and a flow rate of the pumps of the pump assembly according to the present disclosure;

FIG. 14 illustrates graphs of power (y-axis) versus time (x-axis) and temperature (y-axis) versus time (x-axis), respectively, for the same test procedure according to the present disclosure;

FIG. 15 illustrates graphs of impedance (y-axis) versus time (x-axis), temperature (y-axis) versus time (x-axis), and power (y-axis) versus time (x-axis), respectively, for three treatment procedures that each utilize an internally-cooled probe assembly with inherently high-power demand and manual feedback control, when no impedance mitigation is implemented according to conventional construction;

FIG. 16 illustrates graphs of impedance (y-axis) versus time (x-axis), temperature (y-axis) versus time (x-axis), and power (y-axis) versus time (x-axis), respectively, for three treatment procedures that each utilize an internally-cooled probe assembly with pump-modulated power control and impedance mitigation are implemented according to the present disclosure, FIG. 17 illustrates one embodiment of a graph of energy (y-axis) versus lesion area (x-axis) to depict various advantages according to the present disclosure, FIG. 18 illustrates another embodiment of a graph of energy (y-axis) versus lesion area (x-axis) to depict various advantages according to the present disclosure, FIG. 19 illustrates one embodiment of a graph of energy (y-axis) versus thermocouple protrusion length (x-axis) to depict various advantages according to the present disclosure, and FIG. 20 illustrates one embodiment of a graph of lesion size (y-axis) versus thermocouple protrusion length (x-axis) to depict various advantages according to the present disclosure.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this invention, a lesion refers to the region of tissue that has been irreversibly damaged as a result of the application of thermal energy, and the invention is not intended to be limited in this regard. Furthermore, for the purposes of this description, proximal generally indicates that portion of a device or system next to or nearer to a user (when the device is in use), while the term distal generally indicates a portion further away from the user (when the device is in use).

Referring now to the drawings, FIG. 1 illustrates a schematic diagram of one embodiment of a system 100 of the present invention. As shown, the system 100 includes a generator 102, a cable 104, first, second, third, and fourth probe assemblies 106 (only one probe assembly is shown), one or more cooling devices 108, a pump cable 110, one or more proximal cooling supply tubes 112 and one or more proximal cooling return tubes 114. As shown in the illustrated embodiment, the generator 102 is a radiofrequency (RF) generator, but may optionally be any power source that may deliver other forms of energy, including but not limited to microwave energy, thermal energy, ultrasound and optical energy. Further, the generator 102 may include a display incorporated therein. The display may be operable to display various aspects of a treatment procedure, including but not limited to any parameters that are relevant to a treatment procedure, such as temperature, impedance, etc. and errors or warnings related to a treatment procedure. If no display is incorporated into the generator 102, the generator 102 may include means of transmitting a signal to an external display. In one embodiment, the generator 102 is operable to communicate with one more devices, for example with one or more of first and second probe assemblies 106 and the one or more cooling devices 108. Such communication may be unidirectional or bidirectional depending on the devices used and the procedure performed.

In addition, as shown, a distal region 124 of the cable 104 may include a splitter 130 that divides the cable 104 into two or more distal ends 136 such that the probe assemblies 106 can be connected thereto. A proximal end 128 of the cable 104 is connected to the generator 102. This connection can be permanent, whereby, for example, the proximal end 128 of the cable 104 is embedded within the generator 102, or temporary, whereby, for example, the proximal end 128 of cable 104 is connected to generator 102 via an electrical connector. The two or more distal ends 136 of the cable 104 terminate in connectors 140 operable to couple to the probe assemblies 106 and establish an electrical connection between the probe assemblies 106 and the generator 102. In alternate embodiments, the system 100 may include a separate cable for each probe assembly 106 being used to couple the probe assemblies 106 to the generator 102. Alternatively, the splitter 130 may include more than two distal ends. Such a connector is useful in embodiments having more than two devices connected to the generator 102, for example, if more than two probe assemblies are being used.

The cooling device(s) 108 may include any means of reducing a temperature of material located at and proximate to one or more of the probe assemblies 106. For example, as shown in FIG. 10, the cooling devices 108 may include a pump assembly 120 having one or more peristaltic pumps 122 operable to circulate a fluid from the cooling devices 108 through one or more proximal cooling supply tubes 112, the probe assemblies 106, one or more proximal cooling return tubes 114 and back to the one or more cooling devices 108. For example, as shown in the illustrated embodiment of FIGS. 10 and 11, the pump assembly 120 includes four peristaltic pumps 122 coupled to a power supply 126. In such embodiments, as shown in FIG. 11, each of the plurality of pumps 122 may be in separate fluid communication with one of the probe assemblies. The fluid may be water or any other suitable fluid. In alternate embodiments, the pump assembly 120 may include only one peristaltic pump or greater than four pumps. In addition, as shown in FIG. 11, each of the pumps 122 may have an independent speed (i.e. RPM) controller 125 that is configured to independent adjust the speed of its respective pump.

Still referring to FIG. 1, the system 100 may include a controller for facilitating communication between the cooling devices 108 and the generator 102. In this way, feedback control is established between the cooling devices 108 and the generator 102. The feedback control may include the generator 102, the probe assemblies 106 and the cooling devices 108, although any feedback between any two devices is within the scope of the present invention. The feedback control may be implemented, for example, in a control module which may be a component of the generator 102. In such embodiments, the generator 102 is operable to communicate bi-directionally with the probe assemblies 106 as well as with the cooling devices 108. In the context of this invention, bi-directional communication refers to the capability of a device to both receive a signal from and send a signal to another device.

As an example, the generator 102 may receive temperature measurements from one or both of the first and second probe assemblies 106. Based on the temperature measurements, the generator 102 may perform some action, such as modulating the power that is sent to the probe assemblies 106. Thus, both probe assemblies 106 may be individually controlled based on their respective temperature measurements. For example, power to each of the probe assemblies 106 can be increased when a temperature measurement is low or decreased when a measurement is high. This variation of power may be different for each probe assembly. In some cases, the generator 102 may terminate power to one or more probe assemblies 106. Thus, the generator 102 may receive a signal (e.g. temperature measurement) from one or both of the first and second probe assemblies 106, determine the appropriate action, and send a signal (e.g. decreased or increased power) back to one or both of the probe assemblies 106. Alternatively, the generator 102 may send a signal to the cooling devices 108 to either increase or decrease the flow rate or degree of cooling being supplied to one or both of the first and second probe assemblies 106.

More specifically, the pumps may communicate a fluid flow rate to the generator 102 and may receive communications from the generator 102 instructing the pumps to modulate this flow rate. In some instances, the peristaltic pumps may respond to the generator 102 by changing the flow rate or turning off for a period of time. With the cooling devices 108 turned off, any temperature sensing elements associated with the probe assemblies 106 would not be affected by the cooling fluid allowing a more precise determination of the surrounding tissue temperature to be made. In addition, when using more than one probe assembly 106, the average temperature or a maximum temperature in the temperature sensing elements associated with probe assemblies 106 may be used to modulate cooling.

In other embodiments, the cooling devices 108 may reduce the rate of cooling or disengage depending on the distance between the probe assemblies 106. For example, when the distance is small enough such that a sufficient current density exists in the region to achieve a desired temperature, little or no cooling may be required. In such an embodiment, energy is preferentially concentrated between first and second energy delivery devices 192 through a region of tissue to be treated, thereby creating a strip lesion. A strip lesion is characterized by an oblong volume of heated tissue that is formed when an active electrode is in close proximity to a return electrode of similar dimensions. This occurs because at a given power, the current density is preferentially concentrated between the electrodes and a rise in temperature results from current density.

The cooling devices 108 may also communicate with the generator 102 to alert the generator 102 to one or more possible errors and/or anomalies associated with the cooling devices 108. For example, if cooling flow is impeded or if a lid of one or more of the cooling devices 108 is opened. The generator 102 may then act on the error signal by at least one of alerting a user, aborting the procedure, and modifying an action.

Still referring to FIG. 1, the proximal cooling supply tubes 112 may include proximal supply tube connectors 116 at the distal ends of the one or more proximal cooling supply tubes 112. Additionally, the proximal cooling return tubes 114 may include proximal return tube connectors 118 at the distal ends of the one or more proximal cooling return tubes 114. In one embodiment, the proximal supply tube connectors 116 are female luer-lock type connectors and the proximal return tube connectors 118 are male luer-lock type connectors although other connector types are intended to be within the scope of the present invention.

In addition, as shown in FIGS. 1 and 2, the probe assembly 106 may include a proximal region 160, a handle 180, a hollow elongate shaft 184, and a distal tip region 190 that includes the one or more energy delivery devices 192. Further, as shown, the proximal region 160 includes a distal cooling supply tube 162, a distal supply tube connector 166, a distal cooling return tube 164, a distal return tube connector 168, a probe assembly cable 170, and a probe cable connector 172. In such embodiments, the distal cooling supply tube 162 and distal cooling return tube 164 are flexible to allow for greater maneuverability of the probe assemblies 106, but alternate embodiments with rigid tubes are possible.

Further, in several embodiments, the distal supply tube connector 166 may be a male luer-lock type connector and the distal return tube connector 168 may be a female luer-lock type connector. Thus, the proximal supply tube connector 116 may be operable to interlock with the distal supply tube connector 166 and the proximal return tube connector 118 may be operable to interlock with the distal return tube connector 168.

The probe cable connector 172 may be located at a proximal end of the probe assembly cable 170 and may be operable to reversibly couple to one of the connectors 140, thus establishing an electrical connection between the generator 102 and the probe assembly 106. The probe assembly cable 170 may include one or more conductors depending on the specific configuration of the probe assembly 106. For example, in one embodiment, the probe assembly cable 170 may include five conductors allowing probe assembly cable 170 to transmit RF current from the generator 102 to the one or more energy delivery devices 192 as well as to connect multiple temperature sensing elements to the generator 102 as discussed below.

The energy delivery devices 192 may include any means of delivering energy to a region of tissue adjacent to the distal tip region 190. For example, the energy delivery devices 192 may include an ultrasonic device, an electrode or any other energy delivery means and the invention is not limited in this regard. Similarly, energy delivered via the energy delivery devices 192 may take several forms including but not limited to thermal energy, ultrasonic energy, radiofrequency energy, microwave energy or any other form of energy. For example, in one embodiment, the energy delivery devices 192 may include an electrode. The active region of the electrode may be 2 to 20 millimeters (mm) in length and energy delivered by the electrode is electrical energy in the form of current in the RF range. The size of the active region of the electrode can be optimized for placement within an intervertebral disc, however, different sizes of active regions, all of which are within the scope of the present invention, may be used depending on the specific procedure being performed. In some embodiments, feedback from the generator 102 may automatically adjust the exposed area of the energy delivery device 192 in response to a given measurement such as impedance or temperature. For example, in one embodiment, the energy delivery devices 192 may maximize energy delivered to the tissue by implementing at least one additional feedback control, such as a rising impedance value.

Referring now to FIG. 3, the distal cooling supply tube 162 and the distal cooling return tube 164 may be connected to a shaft supply tube 302 and a shaft return tube 304, respectively, within the handle 180, using connecting means 301 and 303. The connecting means 301, 303 can be any means of connecting two tubes including but not limited to ultraviolet (UV) glue, epoxy or any other adhesive as well as friction or compression fitting. Arrows 312 and 314 indicate the direction of flow of a cooling fluid supplied by the cooling devices 108. More specifically, in one embodiment, the shaft supply tube 302 and the shaft return tube 304 may be hypotubes made of a conductive material such as stainless steel that extend from the handle 180 through a lumen of the hollow elongate shaft 184 to distal tip region 190, as shown in FIG. 4, wherein arrow 408 indicates the direction of the cooling fluid flow within a lumen 450 defined by the energy delivery devices 192. The number of hypotubes used for supplying cooling fluid and the number used for returning cooling fluid and the combination thereof may vary and all such combinations are intended to be within the scope of the present invention.

Referring still to FIG. 3, the handle 180 may be at least partially filled with a filling agent 320 to lend more strength and stability to handle 180 as well as to hold the various cables, tubes and wires in place. The filling agent 320 may be epoxy or any other suitable material. In addition, the handle 180 may be operable to easily and securely couple to an optional introducer tube (discussed below) in one embodiment where an introducer tube would facilitate insertion of the one or more probe assemblies 106 into a patient's body. For example, as shown, the handle 180 may taper at its distal end to accomplish this function, i.e. to enable it to securely couple to an optional introducer tube.

In one embodiment, the elongate shaft 184 may be manufactured out of polyimide sheath and a stainless steel tubular interior, which provides exceptional electrical insulation while maintaining sufficient flexibility and compactness. In alternate embodiments, the elongate shaft 184 may be any other material imparting similar qualities. In still other embodiments, the elongate shaft 184 may be manufactured from an electrically conductive material and may be covered by an insulating material so that delivered energy remains concentrated at the energy delivery device 192 of the distal tip region 190. In one embodiment, the probe assembly 106 may also include a marker 384 at some point along the handle 180 or along the length of the elongate hollow shaft 184. In such embodiments, the marker 384 may be a visual depth marker that functions to indicate when the distal tip of the probe assembly 106 is located at a distal end of the introducer tube by aligning with a hub of the introducer tube. The marker 384 will thus provide a visual indication as to the location of the distal tip of a probe assembly 106 relative to an optional introducer tube.

Referring in detail to FIG. 4, a perspective cut-away view of one embodiment of the distal tip region 190 of the probe assembly 106 is illustrated. As shown, the distal tip region 190 includes one or more temperature sensing elements 402 which are operable to measure the temperature at and proximate to the one or more energy delivery devices 192. The temperature sensing elements 402 may include one or more thermocouples, thermometers, thermistors, optical fluorescent sensors or any other means of sensing temperature. In one embodiment, the temperature sensing elements 402 are connected to the generator 102 via probe assembly cable 170 and cable 104 although any means of communication between the temperature sensing elements 402 and the generator 102, including wireless protocols, are included within the scope of the present invention. More specifically, as shown, the temperature sensing element(s) 402 may include a thermocouple junction made by joining a stainless steel hypotube 406 to a constantan wire 410, wherein the constantan wire 410 is insulated by insulation 412. In this embodiment, the junction of hypotube 406 and the constantan wire 410 is made by laser welding, although any other means of joining two metals may be used. Furthermore, in this embodiment, the hypotube 406 and the constantan wire 410 extend through a lumen of the elongate shaft 184 and connect to the probe assembly cable 170 within the handle 180.

Further, as shown particularly in FIGS. 4-6, the temperature sensing element 402 of each probe 106 protrudes beyond the energy delivery device 192. More specifically, as shown, the temperature sensing element 402 may have a length 414 of less than about 1 millimeter (mm) that extends from a distal end 194 of the energy delivery device 192. In addition, as shown particularly in FIG. 6, the length 414 of the temperature sensing element 402 element may be chosen to assist in creating lesions of different sizes. For example, in such embodiments, a user may select one or more probes from a plurality of probes having different lengths 414 based on, e.g. a desired lesion size and/or a desired rate of power delivery based on a treatment procedure type of the tissue. In particular embodiments, the different lengths of the temperature sensing elements 402 may range from about 0.20 mm to about 0.70 mm. In additional embodiments, each of the temperature sensing elements 402 may also have a different shape or volume. Thus, since an actual lesion size will vary with the different lengths 414 of the temperature sensing elements 402, temperature sensing elements 402 having longer lengths (e.g. probes (C) and (D)) are configured to generate lesions of smaller sizes, whereas temperature sensing elements 402 having shorter lengths (e.g. probes (A) and (B)) are configured to generate lesions of larger sizes.

Accordingly, the different lengths of the temperature sensing elements 402 are configured to control and optimize the size of the lesion for different anatomical locations, for instance creating smaller lesions in regions adjacent to critical structures such as arteries and motor nerves. Thus, the different lengths of the temperature sensing elements 402 of the present disclosure provide several advantages including for example, the ability to create custom lesion volumes for different procedures (i.e. the control of the lesion volume is intrinsic to the mechanical design of the probe, which is independent of the generator 102 and algorithms). As such, existing equipment and settings can be used. In addition, the protrusion distance can be optimized to provide maximum energy output while minimizing rising impedance and power roll-off conditions. Moreover, the different lengths of the temperature sensing elements 402 creates a mechanical safety mechanism to prevent over-ablation in sensitive anatomical regions.

In addition, the length 414 of the temperature sensing element 402 is configured to increase (or decrease) a power demand of the energy delivery device 192. Further, as shown, whereby the temperature sensing element 402 includes a stainless steel hypotube 406, the hypotube 406 may be electrically conductive and may be electrically coupled to the energy delivery device 192. Thus, in such an embodiment, whereby energy may be conducted to the protrusion and delivered from the protrusion to surrounding tissue, the protrusion may be understood to be a component of both temperature sensing element 402 as well as the one or more energy delivery devices 192. Placing the temperature sensing elements 402 at this location, rather than within a lumen 450 defined by the energy delivery device 192, is beneficial because it allows the temperature sensing element 402 to provide a more accurate indication of the temperature of tissue proximate to the energy delivery device 192. This is due to the fact that, when extended beyond the energy delivery device 192, the temperature sensing element 402 will not be as affected by the cooling fluid flowing within the lumen 450 as it would be were it located within lumen 450. Thus, in such embodiments, the probe assembly 106 includes a protrusion protruding from the distal region of the probe assembly, whereby the protrusion is a component of the temperature sensing element 402.

Referring still to FIG. 4, the probe assembly 106 may further include one or more secondary temperature sensing elements 404 located within the elongate shaft 184 at some distance away from the energy delivery device 192, and positioned adjacent a wall of the elongate shaft 184. The secondary temperature sensing elements 404 may similarly include one or more thermocouples, thermometers, thermistors, optical fluorescent sensors or any other means of sensing temperature. For example, as shown, the secondary temperature sensing element 404 is a thermocouple made by joining copper and constantan thermocouple wires, designated as 420 and 422 respectively. Further, in certain embodiments, the copper and constantan wires 420 and 422 may extend through a lumen of the elongate shaft 184 and may connect to the probe assembly cable 170 within the handle 180.

In addition, the probe assembly 106 may further include a thermal insulator 430 located proximate to any of the temperature sensing elements 402, 404. As such, the thermal insulator 430 may be made from any thermally insulating material, for example silicone, and may be used to insulate any temperature sensing element from other components of the probe assembly 106, so that the temperature sensing element will be able to more accurately measure the temperature of the surrounding tissue. More specifically, as shown, the thermal insulator 430 is used to insulate the temperature sensing element 404 from cooling fluid passing through the shaft supply tube 302 and the shaft return tube 304.

In further embodiments, the probe assembly 106 may also include a radiopaque marker 440 incorporated somewhere along the elongate shaft 184. For example, as shown, in FIG. 4, an optimal location for a radiopaque marker may be at or proximate to the distal tip region 190, adjacent the energy delivery device 192. The radiopaque markers are visible on fluoroscopic x-ray images and can be used as visual aids when attempting to place devices accurately within a patient's body. These markers can be made of many different materials, as long as they possess sufficient radiopacity. Suitable materials include, but are not limited to silver, gold, platinum and other high-density metals as well as radiopaque polymeric compounds. Various methods for incorporating radiopaque markers into or onto medical devices may be used, and the present invention is not limited in this regard.

Referring now to FIGS. 7 and 8, cross-sectional views of portions of the distal tip region 190, as indicated in FIG. 4, are illustrated. Referring first to FIG. 7, three hypotubes 302, 304, and 406 are positioned within the lumen 450 defined by the elongate shaft 184 and the energy delivery device 192. The shaft supply tube 302 and the shaft return tube 304 carry cooling fluid to and from the distal end of distal tip region 190, respectively. In this embodiment, hypotube 406 is made of a conductive material such as stainless steel and is operable to transmit energy from the probe assembly cable 170 to the energy delivery device 192. In addition, the hypotube 406 defines a lumen within which a means of connecting the one or more temperature sensing elements 402 to the probe assembly cable 170 may be located. For example, if the one or more temperature sensing elements 402 includes a thermocouple, then a constantan wire 410 may extend from probe assembly cable 170 to the thermocouple junction through hypotube 406 as is shown in FIG. 4. Alternatively, more than one wire may be passed through the lumen of hypotube 406 or the lumen of hypotube 406 may be utilized for another purpose.

Further, as shown, the elongate shaft 184 and the electrode 192 overlap to secure the electrode in place. In this embodiment, the lumen defined by the elongate shaft 184 and the electrode 192 at this portion of the distal tip region 190 contains a radiopaque marker 440 made of silver solder, which fills the lumen such that any cooling fluid supplied to the probe assembly 106, that is not located within one of the cooling tubes described earlier, is confined to the distal tip region 190 of probe assembly 106. Thus, in such an embodiment, the silver solder may be referred to as a flow impeding structure since it functions to restrict the circulation of fluid to a specific portion (in this case, at least a portion of distal region 190) of the probe assembly 106. In other words, cooling fluid may flow from the cooling devices 108, through the cooling supply tubes to the distal tip region 190 of the probe assembly 106. The cooling fluid may then circulate within the lumen 450 defined by the electrode 192 to provide cooling thereto. As such, the internally-cooled probe as described herein is defined as a probe having such a configuration, whereby a cooling medium does not exit probe assembly 106 from a distal region of probe assembly 106. The cooling fluid may not circulate further down the elongate shaft 184 due to the presence of the silver solder, and flows through the cooling return tubes back to the cooling devices 108. In alternate embodiments, other materials may be used instead of silver solder, and the invention is not limited in this regard. As described above, providing cooling to the probe assemblies 106 allows heat delivered through the energy delivery devices 192 to be translated further into the tissue without raising the temperature of the tissue immediately adjacent the energy delivery device 192.

Referring now to FIG. 8, a cross-section of a portion of the distal tip region 190, proximal from the cross-section of FIG. 7 as illustrated in FIG. 4, is illustrated. As shown, the secondary temperature sensing element 404 is located proximate to an inner wall of the elongate shaft 184. This proximity allows the secondary temperature sensing element 404 to provide a more accurate indication of the temperature of surrounding tissue. In other words, the secondary temperature sensing element 404 may be operable to measure the temperature of the inner wall of the elongate shaft 184 at the location of the secondary temperature sensing element 404. This temperature is indicative of the temperature of tissue located proximate to the outer wall of the elongate shaft 184. Thus, it is beneficial to have the secondary temperature sensing element 404 located proximate to an inner wall of the elongate shaft 184, rather than further away from the inner wall.

FIGS. 7 and 8 also illustrate the relative positions of the three hypotubes used in a first embodiment of the present invention. In this embodiment, the three hypotubes are held together in some fashion to increase the strength of probe assembly 106. For example, the three hypotubes may be bound together temporarily or may be more permanently connected using solder, welding or any suitable adhesive means. Various means of binding and connecting hypotubes are well known in the art and the present invention is not intended to be limited in this regard.

As mentioned above, the system 100 of the present invention may further include one or more introducer tubes. Generally, introducer tubes may include a proximal end, a distal end, and a longitudinal bore extending therebetween. Thus, the introducer tubes (when used) are operable to easily and securely couple with the probe assembly 106. For example, the proximal end of the introducer tubes may be fitted with a connector able to mate reversibly with handle 180 of probe assembly 106. An introducer tube may be used to gain access to a treatment site within a patient's body and a hollow elongate shaft 184 of a probe assembly 106 may be introduced to said treatment site through the longitudinal bore of said introducer tube. Introducer tubes may further include one or more depth markers to enable a user to determine the depth of the distal end of the introducer tube within a patient's body. Additionally, introducer tubes may include one or more radiopaque markers to ensure the correct placement of the introducers when using fluoroscopic guidance.

The introducer tubes may be made of various materials, as is known in the art and, if said material is electrically conductive, the introducer tubes may be electrically insulated along all or part of their length, to prevent energy from being conducted to undesirable locations within a patient's body. In some embodiments, the elongate shaft 184 may be electrically conductive, and an introducer may function to insulate the shaft leaving the energy delivery device 192 exposed for treatment. Further, the introducer tubes may be operable to connect to a power source and may therefore form part of an electrical current impedance monitor (wherein at least a portion of the introducer tube is not electrically insulated). Different tissues may have different electrical impedance characteristics and it is therefore possible to determine tissue type based on impedance measurements, as has been described. Thus, it would be beneficial to have a means of measuring impedance to determine the tissue within which a device is located. In addition, the gauge of the introducer tubes may vary depending on the procedure being performed and/or the tissue being treated. In some embodiments, the introducer tubes should be sufficiently sized in the radial dimension so as to accept at least one probe assembly 106. In alternative embodiments, the elongate shaft 184 may be insulated so as not to conduct energy to portions of a patient's body that are not being treated.

The system may also include one or more stylets. A stylet may have a beveled tip to facilitate insertion of the one or more introducer tubes into a patient's body. Various forms of stylets are well known in the art and the present invention is not limited to include only one specific form. Further, as described above with respect to the introducer tubes, the stylets may be operable to connect to a power source and may therefore form part of an electrical current impedance monitor. In other embodiments, one or more of the probe assemblies 106 may form part of an electrical current impedance monitor. Thus, the generator 102 may receive impedance measurements from one or more of the stylets, the introducer tubes, and/or the probe assemblies 106 and may perform an action, such as alerting a user to an incorrect placement of an energy delivery device 192, based on the impedance measurements.

In one embodiment, the first and second probe assemblies 106 may be operated in a bipolar mode. For example, FIG. 9 illustrates one embodiment of two probe assemblies 106, wherein the distal tip regions 190 thereof are located within an intervertebral disc 800. In such embodiments, electrical energy is delivered to the first and second probe assemblies 106 and this energy is preferentially concentrated therebetween through a region of tissue to be treated (i.e. an area of the intervertebral disc 800). The region of tissue to be treated is thus heated by the energy concentrated between first and second probe assemblies 106. In other embodiments, the first and second probe assemblies 106 may be operated in a monopolar mode, in which case an additional grounding pad is required on the surface of a body of a patient, as is known in the art. Any combination of bipolar and monopolar procedures may also be used. It should also be understood that the system may include more than two probe assemblies. For example, in some embodiments, three probe assemblies may be used and the probe assemblies may be operated in a triphasic mode, whereby the phase of the current being supplied differs for each probe assembly.

In further embodiments, the system may also be configured to control one or more of the flow of current between electrically conductive components and the current density around a particular component. For example, a system of the present invention may include three electrically conductive components, including two of similar or identical dimensions and a third of a larger dimension, sufficient to act as a dispersive electrode. Each of the electrically conductive components should beneficially be operable to transmit energy between a patient's body and a power source. Thus, two of the electrically conductive components may be probe assemblies while the third electrically conductive component may function as a grounding pad or dispersive/return electrode. In one embodiment, the dispersive electrode and a first probe assembly are connected to a same electric pole while a second probe assembly is connected to the opposite electric pole. In such a configuration, electrical current may flow between the two probe assemblies or between the second probe assembly and the dispersive electrode. To control the current to flow preferentially to either the first probe assembly or the dispersive electrode, a resistance or impedance between one or more of these conductive components (i.e. the first probe assembly and the dispersive electrode) and a current sink (e.g. circuit 'ground') may be varied. In other words, if it would be desirable to have current flow preferentially between the second probe assembly and the dispersive electrode (as in a monopolar configuration), then the resistance or impedance between the first probe assembly and the circuit 'ground' may be increased so that the current will prefer to flow through the dispersive electrode to 'ground' rather than through the first probe assembly (since electrical current preferentially follows a path of least resistance). This may be useful in situations where it would be desirable to increase the current density around the second probe assembly and/or decrease the current density around the first probe assembly. Similarly, if it would be desirable to have current flow preferentially between the second probe assembly and the first probe assembly (as in a bipolar configuration), then the resistance or impedance between the dispersive electrode and 'ground' may be increased so that the current will prefer to flow through the first probe assembly to 'ground' rather than through the dispersive electrode. This would be desirable when a standard bipolar lesion should be formed. Alternatively, it may desirable to have a certain amount of current flow between the second probe assembly and the first probe assembly with the remainder of current flowing from the second probe assembly to the dispersive electrode (a quasi-bipolar configuration). This may be accomplished by varying the impedance between at least one of the first probe assembly and the dispersive electrode, and 'ground', so that more or less current will flow along a desired path. This would allow a user to achieve a specific, desired current density around a probe assembly. Thus, this feature of the present invention may allow a system to be alternated between monopolar configurations, bipolar configurations or quasi-bipolar configurations during a treatment procedure.

Referring now to FIG. 12, a flow diagram of one embodiment of a method 500 for treating tissue of a patient's body, such as an intervertebral disc 800, using the probe assemblies described herein is illustrated. As shown at 502, the method may first include preparing the cooled radiofrequency probe assembly 106 for use to treat tissue of a patient's body. For example, as shown at 504, preparing the cooled radiofrequency probe assembly 106 to treat the tissue may include determining a desired lesion size (or volume) and/or a rate of power delivery required to treat the tissue. Further, as shown at 506, a user may select one or more probes 106 from a plurality of probes based on the length 414 of the temperature sensing element 402 thereof that achieves the desired lesion size or the desired rate of power delivery.

Once the appropriate probe assembly(ies) 106 have been selected having the temperature sensing element(s) 402 of a determined length, as shown at 508, the method 500 includes positioning the probe assembly(ies) 106 into the patient's body. More specifically, the method 500 may generally include inserting the energy delivery device(s) 192 into the patient's body and routing the energy delivery device(s) 192 to the tissue of the patient's body. For example, in one embodiment, with a patient lying on a radiolucent table, fluoroscopic guidance may be used to percutaneously insert an introducer with a stylet to access the posterior of an intervertebral disc. In addition to fluoroscopy, other aids, including but not limited to impedance monitoring and tactile feedback, may be used to assist a user to position the introducer or probe assembly(ies) 106 within the patient's body. The use of impedance monitoring has been described herein, whereby a user may distinguish between tissues by monitoring impedance as a device is inserted into the patient's body. With respect to tactile feedback, different tissues may offer different amounts of physical resistance to an insertional force. This allows a user to distinguish between different tissues by feeling the force required to insert a device through a given tissue. One method of accessing the disc is the extrapedicular approach in which the introducer passes just lateral to the pedicle, but other approaches may be used. A second introducer with a stylet may then be placed contralateral to the first introducer in the same manner, and the stylets are removed. Thus, the probe assemblies 106 can be inserted into each of the two introducers placing the electrodes 192 in the tissue at suitable distances, such as from about 1 mm to about 55 mm.

As shown at 510, the method 500 includes coupling a power source (e.g. the generator 102) to the probe assembly(ies) 106. Once in place, a stimulating electrical signal may be emitted from either of the electrodes 192 to a dispersive electrode or to the other electrode 192. This signal may be used to stimulate sensory nerves where replication of symptomatic pain would verify that the disc is pain-causing. In addition, as shown at 512, since the probe assembly(ies) 106 are connected to the RF generator 102 as well as to peristaltic pumps 122, the method 500 includes simultaneously circulating the cooling fluid through the internal lumens 302, 304 via the peristaltic pumps 122 and delivering energy from the RF generator 102 to the tissue through the energy delivery devices 192. In other words, radiofrequency energy is delivered to the electrodes 192 and the power is altered according to the temperature measured by temperature sensing element 402 in the tip of the electrodes 192 such that a desired temperature is reached between the distal tip regions 190 of the two probe assemblies 106.

During the procedure, a treatment protocol such as the cooling supplied to the probe assemblies 106 and/or the power transmitted to the probe assemblies 106 may be adjusted and/or controlled to maintain a desirable treatment area shape, size and uniformity. More specifically, as shown at 514, the method 500 includes actively controlling energy delivered to the tissue by controlling both an amount of energy delivered through the energy delivery devices 192 and individually controlling the flow rate of the peristaltic pumps 122. In further embodiments, the generator 102 may control the energy delivered to the tissue based on the measured temperature measured by the temperature sensing element(s) 402 and/or impedance sensors.

More specifically, as shown in FIG. 13, a block diagram of one embodiment of a treatment procedure for actively controlling the energy delivered to the tissue by controlling both the amount of energy delivered through the energy delivery devices 192 and the flow rate of the peristaltic pumps 122 according to the present disclosure is illustrated. As shown at 600, ablation is initialized. As shown at 602, the energy dosage may be calculated using simple numerical integration techniques. As shown at 604, the calculated energy dosage may then be compared against a preset energy dosage threshold. If the dosage is not satisfied as shown at 606, the procedure continues to 608 to mitigate rising impedance of the internally-cooled probe assemblies 106 during the treatment procedure. More specifically, as shown, one or more procedure parameters are monitored while delivering the energy from the generator 102 to the tissue through the energy delivery devices 192. The procedure parameter(s) described herein may include, for example, a temperature of the tissue, an impedance of the tissue, a power demand of the energy delivery device 192, or similar, or combinations thereof. Further, as shown, the procedure parameter(s) 608 may be fed into a rising impedance detection engine 610. As shown at 612, the rising impedance detection engine 610 is configured to determine, e.g. in real-time, whether a rising impedance event is likely to occur in a predetermined time period (i.e. whether the rising impedance event is imminent) based on the received procedure parameter(s) 608. The rising impedance detection engine 610 can then determine a command for the pump assembly 120 based on whether the rising impedance event is likely to occur in the predetermined time period.

If not imminent, as shown at 614, the cooling rate can be increased, e.g. by increasing the pump speed (e.g. via the RPM controllers 125) of the peristaltic pumps 122 as shown at 616. After the cooling rate is increased, the ablation 600 continues. If a rising impedance event is imminent, as shown at 618, the cooling rate can be reduced, e.g. by decreasing the pump speed (e.g. via the RPM controllers 125) of the peristaltic pumps 122 as shown at 620. In other words, in several embodiments, the peristaltic pumps 122 may be independently controlled via their respective RPM controllers 125 to alter the rate of cooling to each electrode 192 of the probe assemblies 106. In such embodiments, the power supply 126 of the pump assembly 120 may be decoupled, at least in part, from the generator 102. Further, as shown, the system 550 operates using closed-loop feedback control 634, 636. As used herein, closed loop feedback control refers to control whereby the generator 102 controls the flow rate to the probes via the peristaltic pumps 122 in order to modulate the power to a set point independent of temperature. Alternatively, closed loop feedback may also refer to control whereby the generator 102 controls the flow rate to the probes via the peristaltic pumps 122 in order to modulate the power to achieve desired total delivered energy into the tissue.

Once the energy dosage threshold is satisfied, as shown at 622, the treatment procedure is configured to check if the thermal dosage threshold has been satisfied as shown at 624. If the thermal dosage has not been satisfied, as shown at 626, the treatment procedure proceeds through the independent temperature-power feedback control loop as shown at 628. More specifically, in certain embodiments, the amount of energy delivered through the energy delivery device 192 may be controlled by defining a predetermined threshold temperature for treating the tissue, ramping up the temperature of the tissue via the generator 102 through the energy delivery device 192 to the predetermined threshold temperature, and maintaining the temperature of the tissue at the predetermined threshold temperature to create a lesion in the tissue. In such embodiments, the temperature of the tissue may be maintained at the predetermined threshold temperature as a function of at least one of a power ramp rate, an impedance level, an impedance ramp rate, and/or a ratio of impedance to power.

Only when the thermal dosage threshold has been satisfied, as shown at 630, the procedure terminates as shown at 632. Thus, the system and method of the present disclosure provides the unique features of probe(s) with inherently high-power demand (i.e. short thermocouple protrusion), a pump-modulated power algorithm, a preset energy dosage or total average power threshold, and/or a rising impedance detection engine 610.

Referring now to FIG. 14, graphs of power (y-axis) versus time (x-axis) and temperature (y-axis) versus time (x-axis) for the same test procedure are depicted to illustrate advantages of modulating power based on the rate of cooling. More specifically, as shown, the ablation is started with the pump assembly 120 set to its nominal speed. At time $T_1$ into the test procedure, the cooling rate supplied to the energy delivery device 192 is decreased step-wise as shown at 650. This results in a decrease of the power demand as shown at 652, while the temperature remains the same as shown at 654. As such, the control for the cooling rate operates as an independent feedback control loop from the primary temperature-power feedback control loop (as shown at 628), the latter being responsible for ramping and maintaining the temperature set-point of the tissue. Thus, the temperature set-point does not change with changes to the cooling rate since the power required to heat the tissue is decoupled from the power required to offset the effects of the cooling.

Referring now to FIGS. 15 and 16, example graphs are depicted to illustrate various advantages of mitigating rising impedance during an internally-cooled probe treatment procedure according to the present disclosure. More specifically, FIG. 15 illustrates graphs of impedance (y-axis) versus time (x-axis), temperature (y-axis) versus time (x-axis), and power (y-axis) versus time (x-axis), respectively, for three treatment procedures that each utilize an internally-cooled probe with inherently high power demand and manual feedback control, when no impedance mitigation is implemented. As shown at 656, the test procedure results in high impedance errors. This results in insufficient thermal dosage and incomplete procedures as shown via the temperature 658. Further, the power demand 660 exceeds the predetermined threshold 662.

In contrast, FIG. 16 illustrates graphs of impedance (y-axis) versus time (x-axis), temperature (y-axis) versus time (x-axis), and power (y-axis) versus time (x-axis), respectively, for three treatment procedures that utilize an internally-cooled probe with pump-modulated power control. Thus, as shown, the test procedure can be fully completed with no high impedance errors. Further, as shown, the temperature achieves the set point. Moreover, as shown in the graph of power (y-axis) versus time (x-axis), the pump speed was slowly ramped from the lowest setting starting at the beginning of the procedure and maintained below a predetermined threshold. It should be understood that the predetermined threshold may be determined using historical testing data, or may be dynamic. In addition to controlling to a power threshold(s), other embodiments may control based on power ramp rate(s) (dP/dt), impedance level(s) (Z), impedance ramp rate(s) (dZ/dt), and/or a ratio of impedance to power. Regardless of the feedback mechanism, all embodiments are configured to determine the likelihood of a rising impedance event and adjust the power demand accordingly by controlling the rate of cooling to the energy delivery devices 192. For example, in several embodiments, the power demand of the energy delivery device may be compared to a predetermined threshold. If the power demand is greater than the predetermined threshold, the rising impedance engine 610 may decrease a speed of the pump assembly 120. If the power demand is less than the predetermined threshold, the rising impedance engine 610 may increase the speed of the pump assembly 120.

Following treatment, energy delivery and cooling may be stopped and the probe assemblies 106 are removed from the introducers, where used. A fluid such as an antibiotic or contrast agent may be injected through the introducers, followed by removal of the introducers. Alternatively, the distal tips of the probe assemblies 106 may be sharp and sufficiently strong to pierce tissue so that introducers may not be required. As mentioned above, positioning the probe assemblies 106, and more specifically the energy delivery devices 192, within the patient's body, may be assisted by various means, including but not limited to fluoroscopic imaging, impedance monitoring and tactile feedback. Additionally, some embodiments of this method may include one or more steps of inserting or removing material into a patient's body. For example, as has been described, a fluid may be inserted through an introducer tube during a treatment procedure. Alternatively, a substance may be inserted through the probe assembly 106, in embodiments where probe assembly 106 includes an aperture in fluid communication with a patient's body. Furthermore, material may be removed from the patient's body during the treatment procedure. Such material may include, for example, damaged tissue, nuclear tissue and bodily fluids. Possible treatment effects include, but are not limited to, coagulation of nerve structures (nociceptors or nerve fibers), ablation of collagen, biochemical alteration, upregulation of heat shock proteins, alteration of enzymes, and alteration of nutrient supply.

Referring now to FIG. 17, a graph 700 of energy (y-axis) versus lesion area (x-axis) is provided to illustrate further advantages of the present disclosure. More specifically, as shown, the graph 700 provides energy versus lesion area for three different treatment procedures. Assuming a perfectly spherical lesion volume, a predetermined desired diameter lesion is represented by the vertical dashed line 702. A first test procedure 704 created a lesion using a conventional thermal dosage approach. A second test procedure 708 created a lesion with a shorter ablation time but without pump-modulated power control. A third test procedure 706 created a lesion with a shorter ablation time and pump-modulated power control. As shown via data 708, by running the ablation for a shorter time, a lesion of sufficient size cannot be created. However, if pump-modulated power control is also implemented (as illustrated by results 706), lesions can be created on the order of using the conventional thermal dosage approach as represented by data 704. Thus, by controlling the temperature and the energy delivery rate (i.e. by modulating the pumps 122), the energy delivery rate can be maximized, thereby result in a much faster ablation time. In certain instances, the ablation time can be reduced by as much as half when compared to conventional ablation techniques.

Referring now to FIG. 18, a graph 800 depicting the high correlation 19 between delivered energy (y-axis) and lesion size (x-axis) is illustrated. More specifically, as shown, the lesion width 802 is illustrated by solid dots and the lesion length 804 is represented by hollow dots. FIG. 19 illustrates a graph 850 depicting the inverse correlation between thermocouple protrusion lengths (x-axis) and the total delivered energy (y-axis). In addition, FIG. 20 illustrates a graph 900 depicting the correlation between lesion size (y-axis) and thermocouple protrusion distance (x-axis). Taken together, FIGS. 18-20 demonstrate the effects that the thermocouple protrusion length or distance can have on the generated lesion size through controlling the amount of delivered energy into the tissue. More specifically, thermocouple protrusion length and lesion size are inversely correlated. As such, this characteristic can be exploited to generate various lesion sizes targeting different anatomical locations.

A system of the present invention may be used in various medical procedures where usage of an energy delivery device may prove beneficial. Specifically, the system of the present invention is particularly useful for procedures involving treatment of back pain, including but not limited to treatments of tumors, intervertebral discs, facet joint denervation, sacroiliac joint lesioning or intraosseous (within the bone) treatment procedures. Moreover, the system is particularly useful to strengthen the annulus fibrosus, shrink annular fissures and impede them from progressing, cauterize granulation tissue in annular fissures, and denature pain-causing enzymes in nucleus pulposus tissue that has migrated to annular fissures. Additionally, the system may be operated to treat a herniated or internally disrupted disc with a minimally invasive technique that delivers sufficient energy to the annulus fibrosus to breakdown or cause a change in function of selective nerve structures in the intervertebral disc, modify collagen fibrils with predictable accuracy, treat endplates of a disc, and accurately reduce the volume of intervertebral disc tissue. The system is also useful to coagulate blood vessels and increase the production of heat shock proteins.

Using liquid-cooled probe assemblies 106 with an appropriate feedback control system as described herein also contributes to the uniformity of the treatment. The cooling distal tip regions 190 of the probe assemblies 106 helps to prevent excessively high temperatures in these regions which may lead to tissue adhering to the probe assemblies 106 as well as an increase in the impedance of tissue surrounding the distal tip regions 190 of the probe assemblies 106. Thus, by cooling the distal tip regions 190 of the probe assemblies 106, higher power can be delivered to tissue with a minimal risk of tissue charring at or immediately surrounding the distal tip regions 190. Delivering higher power to energy delivery devices 192 allows tissue further away from the energy delivery devices 192 to reach a temperature high enough to create a lesion and thus the lesion will not be limited to a region of tissue immediately surrounding the energy delivery devices 192 but will rather extend preferentially from a distal tip region 190 of one probe assembly 106 to the other.

As has been mentioned, a system of the present invention may be used to produce a relatively uniform lesion substantially between two probe assemblies 106 when operated in a bipolar mode. Oftentimes, uniform lesions may be contraindicated, such as in a case where a tissue to be treated is located closer to one energy delivery device 192 than to the other. In cases where a uniform lesion may be undesirable, using two or more cooled probe assemblies 106 in combination with a suitable feedback and control system may allow for the creation of lesions of varying size and shape. For example, preset temperature and/or power profiles that the procedure should follow may be programmed into the generator 102 prior to commencement of a treatment procedure. These profiles may define parameters (these parameters would depend on certain tissue parameters, such as heat capacity, etc.) that should be used to create a lesion of a specific size and shape. These parameters may include, but are not limited to, maximum allowable temperature, ramp rate (i.e. how quickly the temperature is raised) and the rate of cooling flow, for each individual probe. Based on temperature or impedance measurements performed during the procedure, various parameters, such as power or cooling, may be modulated, to comply with the preset profiles, resulting in a lesion with the desired dimensions.

Similarly, it is to be understood that a uniform lesion can be created, using a system of the present invention, using many different pre-set temperature and/or power profiles which allow the thermal dose across the tissue to be as uniform as possible, and that the present invention is not limited in this regard.

It should be noted that the term radiopaque marker as used herein denotes any addition or reduction of material that increases or reduces the radiopacity of the device. Furthermore, the terms probe assembly, introducer, stylet etc. are not intended to be limiting and denote any medical and surgical tools that can be used to perform similar functions to those described. In addition, the invention is not limited to be used in the clinical applications disclosed herein, and other medical and surgical procedures wherein a device of the present invention would be useful are included within the scope of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method of treating tissue of a patient's body, the method comprising:
    providing a power source coupled to at least one probe assembly, the at least one probe assembly comprising an elongate member with a distal region and a proximal region, the distal region having an electrically and thermally-conductive energy delivery device for delivering one of electrical and radiofrequency energy to the patient's body, the electrically and thermally-conductive energy delivery device having one or more internal lumens for circulating a cooling fluid therethrough and an electrically and thermally-conductive protrusion having a temperature sensing element, the temperature sensing element extending from a distal end of the energy delivery device;
    inserting the energy delivery device of the at least one probe assembly into the patient's body;
    routing the energy delivery device of the at least one probe assembly to the tissue of the patient's body;
    simultaneously circulating the cooling fluid through the one or more internal lumens via at least one pump assembly and delivering energy from the power source to the tissue through the energy delivery device;
    monitoring one or more procedure parameters while delivering the energy from the power source to the tissue through the energy delivery device;
    determining, in real-time, whether a rising impedance event is likely to occur in a predetermined time period based on the one or more procedure parameters including at least one of a temperature of the tissue, an impedance of the tissue, and a power demand of the energy delivery device;
    responsive to determining that the rising impedance event is likely to occur in the predetermined time period, decreasing a flow rate of the at least one pump assembly; and
    responsive to determining that the rising impedance event is unlikely to occur in the predetermined time period, increasing the flow rate of the at least one pump assembly up to a predetermined maximum flow rate or rotational speed.

2. The method of claim 1, further comprising measuring the temperature of the tissue using the temperature sensing element.

3. The method of claim 2, wherein the temperature sensing element comprises a length of less than about 1 millimeter (mm) that extends from the distal end of the energy delivery device.

4. The method of claim 1, wherein the at least one pump assembly comprises at least one pump communicatively coupled to at least one control module.

5. The method of claim 4, further comprising:
    comparing the power demand of the energy delivery device to a predetermined threshold; and
    if the power demand is greater than the predetermined threshold, decreasing a speed of the at least one pump; and
    if the power demand is less than the predetermined threshold increasing the speed of the at least one pump up to the predetermined maximum flow rate or rotational speed.

6. The method of claim 4, further comprising decoupling, at least in part, the control module of the at least one pump assembly from the power source.

7. The method of claim 1, wherein delivering energy from the power source to the tissue through the energy delivery device further comprises:
    defining a predetermined threshold temperature for treating the tissue;
    ramping up a temperature of the tissue via the power source through the energy delivery device to the predetermined threshold temperature; and,
    maintaining the temperature of the tissue at the predetermined threshold temperature to create a lesion in the tissue.

8. The method of claim 7, further comprising maintaining the temperature of the tissue at the predetermined threshold temperature as a function of at least one of a power ramp rate, an impedance level, an impedance ramp rate, and/or a ratio of impedance to power.

9. The probe assembly of claim 7, wherein the predetermined threshold temperature is determined based at least in part on historical testing data.

10. The probe assembly of claim 7, wherein the predetermined threshold temperature is determined based at least in part on a preset profile corresponding with a desired lesion size.

11. A medical probe assembly for delivering energy to a patient's body, the probe assembly comprising:
    at least one probe having an elongate member with a distal region and a proximal region, said distal region comprising an electrically non-conductive outer circumferential portion;
    an electrically and thermally-conductive energy delivery device extending distally from said electrically non-conductive outer circumferential portion for delivering one of electrical and radiofrequency energy to the patient's body, said energy delivery device comprising a conductive outer circumferential surface and one or more internal lumens configured for circulating a cooling fluid to a distal end of said energy delivery device;
    an electrically and thermally-conductive protrusion extending from said distal end of said energy delivery device, said electrically and thermally-conductive protrusion being electrically coupled to said energy delivery device, said electrically and thermally-conductive protrusion comprising a temperature sensing element;

at least one pump assembly for circulating the cooling fluid to and from the electrically and thermally-conductive energy delivery device;

one or more sensors for monitoring one or more procedure parameters including at least one of a temperature of the patient's tissue, an impedance of the tissue, and a power demand of the energy delivery device; and a controller communicatively coupled to the one or more sensors, the controller comprises a rising impedance detection engine configured to perform operations comprising:

determining, in real-time, whether a rising impedance event is likely to occur in a predetermined time period based on the one or more procedure parameters, responsive to determining that the rising impedance event is likely to occur in the predetermined time period, decreasing a flow rate of the at least one pump assembly, and responsive to determining that the rising impedance event is unlikely to occur in the predetermined time period, increasing the flow rate of the at least one pump assembly up to a predetermined maximum flow rate or rotational speed.

12. The probe assembly of claim 11, wherein the temperature sensing element is configured to measure the temperature of the tissue.

13. The probe assembly of claim 12, wherein the temperature sensing element comprises a length of less than about 1 millimeter (mm) that extends from a distal end of the energy delivery device.

14. The probe assembly of claim 11, wherein the at least one pump assembly comprises at least one pump communicatively coupled to at least one control module.

15. The probe assembly of claim 14, wherein the at least one pump assembly comprises a plurality of pumps communicatively coupled to the at least one control module, each of the plurality of pumps in separate fluid communication with a different probe assembly.

16. The probe assembly of claim 11, wherein the controller is further configured to compare the power demand of the energy delivery device to a predetermined threshold, and if the power demand is greater than the predetermined threshold, decrease the speed for the at least one pump, and if the power demand is less than the predetermined threshold, increase the speed for the at least one pump up to the predetermined maximum flow rate or rotational speed.

17. The probe assembly of claim 11, wherein the one or more operations further comprise:

defining a predetermined threshold temperature for treating the tissue;

ramping up a temperature of the tissue via a power source through the energy delivery device to the predetermined threshold temperature; and, maintaining the temperature of the tissue at the predetermined threshold temperature to create a lesion in the tissue.

* * * * *

UNITED STATES PATENT AND TRADEMARK OFFICE
CERTIFICATE OF CORRECTION

Page 1 of 2

PATENT NO. : 12,232,801 B2
APPLICATION NO. : 17/058718
DATED : February 25, 2025
INVENTOR(S) : Ruoya Wang et al.

It is certified that error appears in the above-identified patent and that said Letters Patent is hereby corrected as shown below:

On the Title Page

Item (72), reading:
Inventors: Ruoya Wang, Decatur, GA (US); Jennifer J. Barrett, Alpharetta, GA (US); Joseph DiPietro, Ponte Vedra, FL (US); Rasagnya M. Viswanadha, Cumming, GA (US); Tyler W. Crone, Atlanta, GA (US)
Should Read:
Inventors: Ruoya Wang, Decatur, GA (US); Jennifer J. Barrett, Alpharetta, GA (US); Joseph DiPietro, Ponte Vedra Beach, FL (US); Rasagnya M. Viswanadha, Cumming, GA (US); Tyler W. Crone, Atlanta, GA (US)

In the Specification

Column 1, Lines 8-10, reading:
The present invention claims priority to U.S. Provisional Application No.: 62/677,714 filed on May 30, 2018, which is incorporated herein by reference in its entirety.
Should Read:
The present invention is a national stage entry of International Patent Application No. PCT/US2019/034164 having a filing date of May 28, 2019, which claims priority to U.S. Provisional Application No. 62/677,714, filed on May 30, 2018, both of which are incorporated herein in their entireties by reference thereto.

In the Claims

Column 22, Claim 9, Line 45, reading:
The probe assembly of claim 7, wherein the predeter-
Should Read:
The method of claim 7, wherein the predeter- Signed and Sealed this
Twenty-seventh Day of May, 2025

Coke Morgan Stewart
*Acting Director of the United States Patent and Trademark Office*

CERTIFICATE OF CORRECTION (continued)
U.S. Pat. No. 12,232,801 B2

Column 24, Claim 10, Line 48, reading:
The probe assembly of claim 7, wherein the prede-
Should Read:
The method of claim 1, wherein the prede- Column 24, Claim 17, Lines 21-22, reading:
The probe assembly of claim 11, wherein the one or more operations further comprise:
Should Read:
The probe assembly of claim 11, wherein the operations further comprise: